US010154870B2

(12) United States Patent
Ottanelli

(10) Patent No.: US 10,154,870 B2
(45) Date of Patent: Dec. 18, 2018

(54) DISPENSER OF CRYOGENIC SUBSTANCES, AND A PROCESS FOR DISPENSING THE CRYOGENTIC SUBSTANCES

(71) Applicant: SIXTEM LIFE S.R.L., Sesto Fiorentino (IT)

(72) Inventor: Luciano Ottanelli, Prato (IT)

(73) Assignee: SIXTEM LIFE S.R.L., Florence (IT)

( * ) Notice: Subject to any disclaimer, the term of this patent is extended or adjusted under 35 U.S.C. 154(b) by 374 days.

(21) Appl. No.: 14/648,738

(22) PCT Filed: Nov. 19, 2013

(86) PCT No.: PCT/IB2013/060236
§ 371 (c)(1),
(2) Date: Jun. 1, 2015

(87) PCT Pub. No.: WO2014/083479
PCT Pub. Date: Jun. 5, 2014

(65) Prior Publication Data
US 2015/0313662 A1 Nov. 5, 2015

(30) Foreign Application Priority Data

Nov. 30, 2012 (IT) .............................. MI2012A2050

(51) Int. Cl.
*A61B 18/02* (2006.01)
*B65D 83/20* (2006.01)
(Continued)

(52) U.S. Cl.
CPC ........ *A61B 18/0218* (2013.01); *B65D 83/205* (2013.01); *B65D 83/22* (2013.01);
(Continued)

(58) Field of Classification Search
CPC ...... A61B 18/0218; A61B 2018/00452; A61B 18/02; B65D 2215/02; B65D 2215/04; B65D 83/205; B65D 83/22; B65D 83/303
See application file for complete search history.

(56) References Cited

U.S. PATENT DOCUMENTS 3,848,778 A * 11/1974 Meshberg ............ B65D 83/205
222/402.11
7,757,905 B2 * 7/2010 Strand .................... B65D 83/22
222/153.11
(Continued)

FOREIGN PATENT DOCUMENTS

EP 1904149 B1 9/2010
GB 1163573 9/1969
(Continued)

*Primary Examiner* — Daniel Fowler
*Assistant Examiner* — Tigist Demie
(74) *Attorney, Agent, or Firm* — Nixon & Vanderhye P.C.

(57) ABSTRACT

A method for dispensing cryogenic substances including: predisposing a pressurized container for a cryogenic substance which includes a valve active at the opening and regulating an emission of the cryogenic substance, predisposing a coupling element stably constrained to the container, predisposing an activating element engaged to the coupling element in such a way that it is interposed between the container and the activating element. There may be: a dispensing step in which the activating element is pressed nearingly to the container to bring the valve of the container into a passage condition to enable exit of the cryogenic substance, a safety step in which the activating element is stably blocked to the coupling element, an intermediate step in which the activating element is mobile relatively by rotation with respect to the blocking element to allow passage from the dispensing step to the safety step and vice versa, an unblocking step including elastic deformation of a
(Continued)

part of the activating element which enables passage between the safety step and the intermediate step.

12 Claims, 11 Drawing Sheets

(51) Int. Cl.
*B65D 83/22* (2006.01)
*B65D 83/30* (2006.01)
*A61B 18/00* (2006.01)

(52) U.S. Cl.
CPC .. *B65D 83/303* (2013.01); *A61B 2018/00452* (2013.01); *B65D 2215/02* (2013.01); *B65D 2215/04* (2013.01)

(56) References Cited

U.S. PATENT DOCUMENTS

2010/0042087 A1* 2/2010 Goldboss ........... A61B 18/0218
606/22
2010/0087805 A1 4/2010 Citterio

FOREIGN PATENT DOCUMENTS

WO 2007028975 3/2007
WO 2011045630 A1 4/2011

\* cited by examiner

DISPENSER OF CRYOGENIC SUBSTANCES, AND A PROCESS FOR DISPENSING THE CRYOGENTIC SUBSTANCES

CROSS RELATED APPLICATIONS

This application is the U.S. national phase of International Application No. PCT/IB2013/060236 filed 19 Nov. 2013 which designated the U.S. and claims priority to MI2012A002050 filed 30 Nov. 2012, the entire contents of each of which are hereby incorporated by reference.

FIELD OF INVENTION

The present invention relates to a dispenser of cryogenic substances and a method for dispensing them. The method and dispenser are applicable in the treatment of disorders or illnesses of the skin. In particular, the dispenser, particularly of the spray type, can be used in the field of dermatology for treatment of various pathologies/imperfections of the skin, for example for the topical treatment of verrucas, seborrheic keratosis, skin tags, freckles, cutaneous formations, unaesthetic skin conditions, etc.

STATE OF THE ART

As is known, the use of cryogenics is in continuous expansion in applications in the medical field (for example in cryosurgery and in cryo-conservation). Of particular interest for the following description, is the use of cryogenics in the medical field, in particular in the dermatological field.

In the dermatological field, cryogenic substances (for example liquid nitrogen) widely amply used, as, differently to classic surgical interventions, they usually require no anaesthetic, do not usually create scar tissue, do not require problematic dressings nor long periods of convalescence after treatments.

Of particular interest for the following description are spray devices for dispensing cryogenic substances and the topical treatment of skin imperfections. A first example, described in document WO 2007/028975, concerns a dispensing device of cryogenic substances for treatment of epidermis tissue. The device is constituted by a can on which a dispensing system is arranged, for enabling emission of the cryogenic fluid through a tubular extension which terminates with an applicator proper: the applicators are circular and can exhibit different diameters according to the dimensions of the lesion to be treated. The applicators are, further, removably associated to the device in such a way as to be replaceable.

A second example, described in document US 2010/042087, also concerns a cryogenic device for treatment of skin diseases. The device comprises a can exhibiting a dispensing button on which a dispensing tube is mounted which, on the distal end thereof, exhibits an applicator. The applicator exhibits an engaging portion, able to receive a dispensing cannula, and a truncoconical application section associated to the dispensing cannula at which at least a dispensing piercing for expulsion of cryogenic gases is present.

The second example too specifies the presence of removable applicators, having a different shape and section for treating lesions of different natures and sizes, and made of transparent material for enabling viewing the zone to be treated.

A third example, described in document GB 1 163 573, concerns a cryogenic device for treatment of skin disturbances of the skin in which a substance is dispensed from a spray can by means of a dispensing channel and directed at the zone to be treated. In particular, the document describes a truncoconical applicator in which the distal portion from the application point functions as an escape for the pressurized gas. The third example specifies, similarly to what is described in the above examples, that the device can receive applicators of different dimensions or be used in the inverse shape thereof in such a way as to apply the fluid at the larger diameter of the truncoconical shape. Differently to the above-cited documents, in the third example no reference is made to the possibility of using applicators made of a transparent material.

The devices described in the above examples enable the user to have a good control over the dispensing of the cryogenic substance in outlet from the can thanks to the use of the applicators: the applicators enable using the can at a correct distance from the zone to be treated and dispensing the cryogenic substance at the zone. Further, the possibility of mounting various types of applicators, having a diversified shape and/or dimension, guarantees the above-described devices a good flexibility of use.

However, the above-described devices are not free of drawbacks and limitations. In order better to fully understand the drawbacks of the devices described above, it is useful to specify that the cryogenic treatments require particular precautions given the nature of the substance with which the treatment is carried out; these substances can in fact cause burns, or, if dispensed on unsuitable zones for treatment, cause grave lesions.

The devices briefly analysed in the foregoing do not exhibit a safety system able to effectively prevent an accidental dispensing of the cryogenic substance.

AIM OF THE INVENTION

The aim of the present invention is substantially to obviate at least one of the drawbacks and/or limitation of the prior art.

A first objective of the invention is to provide a method and a dispenser of cryogenic substances of cryogenic substances exhibiting at least a safety system able to prevent accidental dispensing of cryogenic substance.

A further main aim of the invention is to provide a method and a dispenser of cryogenic substances that enable an excellent control of the quantity of substance to be dispensed as well as an excellent dispensing precision.

A further aim of the invention is to provide a method and a dispenser of cryogenic substances exhibiting a high flexibility of use, in particular being usable for various topical treatments.

A further aim of the invention is to provide a dispenser of cryogenic substances composed of a minimum number of components such that the dispenser is simple to realise, easy to use and assemble and constructed with a specific structure that optimises the effectiveness of the treatment.

A further aim of the present invention is to provide a dispenser of cryogenic substances the components of which exhibit a production and assembly cost that is smaller so that the dispenser is economical.

One or more of the above-described aims, which will more fully emerge during the course of the following are substantially attained by a method and a dispenser of cryogenic substances according to one or more of the appended claims.

SUMMARY

Aspects of the invention are described in the following.

A first aspect relates to a dispenser (1) of cryogenic substances (C), comprising:

at least a pressurised container (2) configured such as to contain a predetermined quantity of cryogenic substance (C), the container (2) exhibiting at least an opening (2a) suitable for enabling exit of the cryogenic substance (C) along an expulsion direction (E), the container (2) comprising a valve (3) active at the opening (2a) and configured such as to be arranged in a normally closed condition in which it prevents the exit of the cryogenic substance (C) from the opening (2a), the valve (3) being further configured such as to be arranged, following an activating operation thereof, in a passage condition in which the valve (3) enables exit of the cryogenic substance (C), at least a coupling element (4) comprising a first engaging portion (10) able to stably constrain the coupling element (4) to the container (2) substantially at the opening (2a), the coupling element (4) comprising a second engaging portion (11) emerging from the first engaging portion (10) distancingly with respect thereto, the second engaging portion (11) comprising at least a blocking portion (7) and at least a passage seating (8) angularly offset to one another with respect to an axis (A) that is substantially parallel to the expulsion direction (E), at least an activating element (5) cooperating with the second engaging portion (11) of the coupling element (4) such that the coupling element is interposed between the container (2) and the activating element (5), the activating element (5) comprising a dispensing conduit (6) in fluid communication with the opening (2a) of the container (2) and configured such as to enable emission of the cryogenic substance (C) towards the external environment, the activating element (5) further comprising an active portion (9) able to cooperate with the blocking portion (7) and the passage seating (8) of the coupling element (4), and wherein the activating element (5) is configured so as to define, in cooperation with the coupling element (4) at least following operating conditions:

at least a dispensing condition in which the active portion (9) of the activating element (5) is at the passage seating (8), the activating element (5), in the dispensing condition, being translatable along a sliding direction (S) nearingly to the container (2), the activating element (5), following the nearing along the sliding direction (S) towards the container (2), being configured such as to arrange the valve (3) in the passage condition and consequently enabling exit of at least a part of the cryogenic substance (C) from the opening (2a), at least a safety condition in which a lower appendage (9a) of the activating element (5) is located at the at least a blocking portion (7) of the coupling element (4), the activating element (5), in the safety condition, being stably blocked to the coupling element (4) preventing relative rotations and axial slidings of the activating element (5) with respect to the coupling element (4), at least an intermediate condition in which the activating element (5) is mobile relatively to the coupling element (4) by rotation about the axis (A) substantially parallel to the expulsion direction (E), the activating element (5), in the intermediate condition, being mobile from a dispensing condition to a safety condition and vice versa, the activating element (5) is configured such as to elastically deform, following application of an external stress (F), such as to enable, at least in the safety condition, the decoupling between the lower appendage (9a) of the activating element (5) and the blocking portion (7) of the coupling element (4), the activating element (5), following the application of the external stress (F), being arrangeable in the intermediate condition and consequently being able to pass from the safety condition to at least a dispensing condition.

In a second aspect according to the 1st aspect, when in the safety condition the activating element is not mobile relative to the coupling element (4).

In a 3rd aspect according to any one of the preceding aspects the activating element (5) comprises a body (5c) having at least a thrust portion (5d) located at an external lateral wall (5e) of the body (5c), the thrust portion (5d) being configured such as to receive the external stress (F) directed transversally to the expulsion direction (E), the thrust portion (5d), following the application of the external stress (F), being configured such as to elastically deform at least a portion of the body (5c) in such a way as to enable the distancing of the active portion (9) of the activating element (5) with respect to the blocking portion (7) of the coupling element (4) such as to enable decoupling thereof.

In a 4th aspect according to the preceding aspect the thrust portion (5d) is angularly offset relative to the active portion (9) with respect to the axis (A), in particular being offset by 90° with respect to the active portion (9).

In a 5th aspect according to aspects 3 or 4, the body (5c) comprises two thrust portions (5d) located symmetrically to one another with respect to the axis (A) substantially parallel to the expulsion direction (E).

In a 6th aspect according to any one of the preceding aspect, the coupling element exhibits a shape substantially having a cylindrical symmetry about the expulsion direction (E).

In a 7th aspect according to any one of the preceding aspects the first engaging portion (10) is stably coupled with an engaging portion (2b) of the container (2) positioned at the opening (2a), the second engaging portion (11) being configured such as to stably constrain the activating element (5) to the coupling element (4), the second engaging portion (11) of the coupling element (4) being connected to the first engaging portion (10) of the coupling element (4) and emerging distancingly with respect thereto.

In an 8th aspect according to any one of the preceding aspects the second engaging portion (11) of the coupling element (4) comprise the blocking portion (7), which exhibits at least a projection (15) defining at least a radial intersection portion (13) and a support portion (17).

In a 9th aspect according to any one of aspects from 3 to 8, the body (5c) of the activating element (5) defines a housing compartment (5a) delimited by an internal lateral wall (5b) and containing at least a part of the second engaging portion (11) of the coupling element (4), the active portion (9) of the activating element (5) comprising at least a projection (12) emerging from the internal lateral wall (5b) of the housing compartment (5a) nearingly to the coupling element (4), the projection (12) of the activating element (5) defining at least a radial intersection portion (13) and an axial intersection portion (14).

In a 10th aspect according to the preceding aspect, the radial intersection portion (13) and the axial intersection portion (14) of the activating element (5), during the safety condition, are abutted respectively to the radial intersection portion (16) and the support portion (17) of the coupling element (4), in the safety condition the radial intersection portion (16) and the support portion (17) of the coupling element (4) being configured such as respectively to prevent the rotation and translation of the activating element (5).

In an 11th aspect according to the preceding aspect the radial intersection portion (16) of the coupling element (4) defines a radial undercut with respect to the radial intersection portion (13) of the activating element (5), the radial intersection portion (13) of the activating element (5), during the safety condition, being abutted to the radial intersection portion (16) of the coupling element (4) and blocked in movement with respect thereto.

In a 12th aspect according to any one of claims from 9 to 11, the axial intersection portion (14) of the activating element (5) is abutted to the support portion (17) of the coupling element (4), at least in the safety condition.

In a 13th aspect according to any one of aspects from 9 to 12, the axial intersection portion (14) of the activating element (5) is abutted to the support portion (17) of the coupling element (4) in the safety condition and in the intermediate condition.

In a 14th aspect according to any one of aspects from 8 to 13, the support portion (17) of the coupling element defines an axial undercut able to prevent the activating element (5), at least in the safety condition, from translating along the expulsion direction (E) nearingly to the container (2).

In a 15th aspect according to any one of the preceding aspects, the passage seating (8) of the coupling element (4) is arranged on the second engaging portion (11) thereof and extends substantially parallel to the expulsion direction (E), the passage seating (8) being angularly offset with respect to the blocking portion (7) of the coupling element (4) with respect to the expulsion direction (E).

In a 16th aspect according to any one of aspects from 9 to 15, the passage seating (8) being configured such as to enable passage of the axial intersection portion (14) of the activating element (5), during the dispensing condition, and therefore the sliding of the activating element (5) nearingly to the container (2).

In a 17th aspect according to any one of the preceding aspects, the coupling element (4) comprises two blocking portions (7) located symmetrically to one another with respect to the expulsion direction (E), and wherein the coupling element further comprises (4) two passage seatings (8), also located symmetrically to one another with respect to the expulsion direction (E), the blocking portion (7) and the passage seatings (8) being angularly offset with respect to one another with respect to the expulsion direction (E), in particular being offset by 90° to one another.

In an 18th aspect according to any one of aspects from 8 to 17, the second engaging portion (11) of the coupling element (4) comprises at least a lateral wall (18) extending substantially parallel to the expulsion direction (E), the radial intersection portion (16) of the coupling element (4) emerging radially from the lateral wall (18) towards the internal lateral wall (5b) of the housing compartment (5a), and wherein the support portion (17) of the coupling element (4) is defined by at least a portion of the free end surface of the lateral wall (18) located on an opposite side with respect to the first engaging portion (10) of the coupling element (4).

In a 19th aspect according to any one of aspects from 9 to 18, the projection (12) of the activating element (5) comprises at least a rib (19) emerging substantially parallel to the internal lateral wall (5b) of the housing compartment (5a) nearingly to the coupling element (4), the rib (19) defining the radial intersection portion (14) and the support portion (15) of the activating element (5).

In a 20th aspect according to aspects 18 or 19, the lateral wall (18) of the coupling element (4) exhibits a substantially hollow cylindrical shape, in particular concentric to the expulsion direction (E), and wherein the activating element (5) comprises a first engaging portion (20) constrained to the second engaging portion (11) of the coupling element (4), the engaging portion (20) of the activating element (5) comprising at least an abutment (21) emerging from the internal lateral wall (5b) of the housing compartment (5a) and constrained to the inside of the lateral wall (18) of the coupling element, the lateral wall (18) of the coupling element (4) being configured so as to enable constraining the activating element (5) and the centring thereof on the coupling element (4).

In a 21st aspect according to the preceding aspect the engaging portion (20) of the activating element (5) is at least partially complementarily shaped to the lateral wall (18) of the coupling element (4).

In a 22nd aspect according to any one of the preceding aspects the dispensing conduit (6) of the activating element (5) is arranged internally of the engaging portion (20) thereof, the dispensing conduit (6) being configured so as to arrange the valve (3) in the passage condition, during the translation of the activating element (5) along the expulsion direction (E).

In a 23rd aspect according to any one of the preceding aspects, the activating element (5) is unremovably constrained to the coupling element (4).

In a 24th aspect according to any one of the preceding aspects, the container (2) during the dispensing condition, is configured such as to dispense only a predetermined discrete quantity of cryogenic substance (C) less than the total quantity of cryogenic substance (C) present internally of the container (2).

In a 25th aspect according to the preceding aspect, the container (2) comprises comprises a general chamber (2c) configured such as to contain a predetermined quantity of cryogenic substance (C), the container (2) further comprising a pre-chamber (2d) exhibiting at least an inlet (22) for setting the general chamber (2c) in fluid communication with the pre-chamber (2d), the pre-chamber (2d) further exhibits at least an outlet (23) for setting the pre-chamber (2d) in fluid communication with the opening (2a) of the container (2), the container (2) comprising at least a valve (24) operatively active on the inlet (22) and on the outlet (23) of the pre-chamber (2d), the valve (24), in the dispensing condition, being configured such as to set the pre-chamber (2d) in fluid communication with the opening (2a) of the container (2) and to prevent the passage of fluid between the general chamber (2c) and the inlet (22), the valve (24) of the container (2), in the dispensing condition, being configured such as to enable emission of the predetermined quantity of cryogenic substance (C) present in the pre-chamber (2d) of the opening (2a) of the container (2), and wherein the valve (24), in the safety condition and/or in the intermediate condition, is configured such as to set in fluid communication the pre-chamber (2d) with the general chamber (2c) and prevent the passage of fluid between the pre-chamber (2d) and the opening (2a) of the container (2).

In a 26th aspect according to the preceding aspect, the pre-chamber (2d) exhibits a smaller volume that the volume of the general chamber (2c) and the ratio between the volume of the general chamber (2c) and the volume of the pre-chamber (2d) is greater than 2, in particular greater than 3, still more in particular greater than 4.

In a 27th aspect according to any one of the preceding aspect, the dispenser comprises at least an applicator (25)

having a body (26) extending along a prevalent development direction between a first and a second end (27, 28), the applicator (25) being removably engaged, at the first end (27), to the activating element (5) and emerging from the external lateral wall (5e) thereof in an exiting direction with respect to the housing compartment (5a) of the activating element (5), and wherein the applicator (25) exhibits a through-opening (29) extending internally of all the body (26) from the first end (27) to the second end (28), the dispensing conduit (6) of the activating element (5) being in fluid communication with the opening (29) of the applicator (25), the applicator (25), in the dispensing condition, being configured such as to guide the cryogenic substance (C) arriving from the container (2) towards the outside environment.

In a 28th aspect according to the preceding aspect, the opening (29) defines, at the first and second ends (27, 28), respectively a first and a second passage opening (30, 31), the first passage opening (30) defining a passage area that is smaller than the passage area defined by the second passage opening (31).

In a 29th aspect according to the 27 and 28th aspect the opening (29) exhibits a shape having a cylindrical symmetry about an axis that is substantially parallel to the prevalent development direction of the applicator (25), in particular the opening (29) exhibiting a truncoconical shape having a growing passage section from the first end (27) in the direction of the second end (28).

In a 30th aspect according to aspects 27, 28 or 29, the applicator (25) is removably engaged to the activating element (5).

In a 31st aspect according to any one of aspects from 27 to 30, the applicator (25) is at least in part realised in a transparent material, in particular the applicator (25) is totally made of a transparent material.

In a 32nd aspect according to any one of aspects from 27 to 31, the applicator 25 is at least partly realised in a plastic material, by way of example the applicator (25) being made of at least one of the following materials: polypropylene, polyethylene, PVC.

A 33rd aspect relates to a method for dispensing cryogenic substances (C) comprising following steps:
predisposing at least a pressurised container (2) configured such as to contain a predetermined quantity of cryogenic substance (C), the container (2) exhibiting at least an opening (2a) enabling exit of the cryogenic substance (C) along an expulsion direction (E), the container (2) comprising a valve (3) active at the opening (2a) and configured such as to be arranged in a normally closed condition in which it obstructs exit of the cryogenic substance (C) from the opening (2a), the valve (3) being further configured such as to be arranged, following an activating operation thereof, in a passage condition in which the valve (3) enables exit of the cryogenic substance (C),
predisposing at least a coupling element (4) comprising a first engaging portion (10) able to stably constrain the coupling element (4) to the container (2) substantially at the opening (2a), the coupling element (4) comprising a second engaging portion (11) emerging from the first engaging portion (10) distancingly with respect thereto, the second engaging portion (11) comprising at least a blocking portion (7) and at least a passage seating (8) angularly offset with respect to one another with respect to an axis (A) that is substantially parallel to the expulsion direction (E),
predisposing at least an activating element (5) engaged to the second engaging portion (11) of the coupling element (4) in such a way that the coupling element is interposed between the container (2) and the activating element (5), the activating element (5) comprising a dispensing conduit (6) in fluid communication with the opening (2a) of the container (2) and configured such as to guide the emission of the cryogenic substance (C) into the outside environment, the activating element (5) further comprising an active portion (9) able to cooperate with the blocking portion (7) and the passage seating (8) of the coupling element (4),
and wherein the method comprises following steps:
at least a dispensing step in which the active portion (9) slides in the passage seating (8) along a sliding direction (S) substantially parallel to the expulsion direction (E) and nearingly to the container (2), the activating element (5), following the nearing along the sliding direction (S) towards the container (2), being configured such as to arrange the valve (3) of the container (2) in the passage condition in order to enable exit of at least a part of the cryogenic substance (C) from the opening (2a),
at least a safety blocking step, at least following a dispensing step, in which the active portion (9) of the activating element (5) is abutted to at least a blocking portion (7) of the coupling element (4), the activating element (5), in the safety condition, being stably blocked to the coupling element (4),
at least a step of intermediate movement in which the activating element (5) is mobile relatively to the coupling element (4) by rotation about an axis (A) substantially parallel to the expulsion direction (E), the activating element (5), during the intermediate step, enabling movement from the dispensing step to the safety step and vice versa,
the method comprising a step of unblocking which comprises a step of elastically deforming at least a part of the activating element (5) following application of an external stress (F), the elastic deformation step being configured such as to enable decoupling between the blocking portion (7) of the coupling element (4) and the active portion (9) of the activating element (5) when they are in the safety step such as to enable passage between the safety step and the intermediate step.

In a 34th aspect according to the preceding aspect, during the safety step the activating element is not mobile in relation to the coupling element (4).

In a 35th aspect according to aspects 33 or 34, the activating element (5) comprises a body (5c) comprising at least a thrust portion (5d) located at an external lateral wall (5e) of the body (5c), the elastic deformation step comprising application of the external stress (F), directed transversally to the expulsion direction (E) and having an entering direction with respect to the activating element (5), on the thrust portion (5d), at least a part of the body (5c) of the activating element (5), following the application of the external stress (F), deforming elastically such as to enable distancing and decoupling of the active portion (9) of the activating element (5) with respect to the blocking portion (7) of the coupling element (4).

In a 36th aspect according to the preceding aspect, the thrust portion (5d) is angularly offset relatively to the active portion (9) with respect to the expulsion direction (E), in particular being offset by 90°; the elastic deformation step comprising the application of the external stress (F) at an angularly offset point with respect to the position of the active portion (9) of the activating element (5).

In a 37th aspect according to any one of aspects from 33 to 36, the dispensing step comprises a substep of pushing the activating element (5) nearingly to the container (2), the pushing step including the sliding of the activating element (5) along the sliding direction (S), substantially parallel to the longitudinal direction (E); the step of pushing enables the predisposing of the valve (3) of the container (2) of the passage condition.

In a 38th aspect according to any one of aspects from 33 to 37, the intermediate step include only relative rotation of the activating element (5) with respect to the coupling element (4), during the intermediate step the activating element (5) maintaining a same distance from the container (2).

In a 39th aspect, according to any one of claims from 33 to 38, the coupling element (4) exhibits a substantially cylindrical symmetry about the expulsion direction (E), the first engaging portion (10) being stably coupled with an engaging portion (2b) of the container (2) located at the opening (2a), the second engaging portion (11) of the coupling element (4) being connected to the first engaging portion (10) of the coupling element and emerging distancingly with respect thereto, the blocking portion (7) exhibiting at least a projection (15) defining at least a radial intersection portion (16) and a support portion (17), and wherein the activating element (5) defines a housing compartment (5a) containing at least a part of the second engaging portion (11) of the coupling element (4), the active portion (9) of the activating element (5) comprising at least a projection (12) arranged internally of the housing compartment (5a) and which defines at least a radial intersection portion (13), extending nearingly to the coupling element (4), and wherein during the safety step, the radial intersection portion (13) and the axial intersection portion (14) of the activating element (5) are abutted respectively to the portion of radial intersection (16) and to the support portion (17) of the coupling element (4), during the safety step, the radial intersection portion (16) and the support portion (17) of the coupling element (4) respectively blocking rotation and translation of the activating element (5).

In a 40th aspect according to the preceding aspect, the radial intersection portion (16) of the coupling element (4) defines a radial undercut with respect to the radial intersection portion (13) of the activating element (5), the radial intersection portion (13) of the activating element (5), during the safety step, being abutted to the radial intersection portion (16) of the coupling element (4) and blocked thereby.

In a 41st aspect according to aspects 39 or 40, at least during the step the safety step the axial intersection portion (14) of the activating element (5) is abutted to the support portion (17) of the coupling element (4) at least in the safety condition, during the safety step the support portion (17) defines an axial undercut able to prevent the activating element (5) from translating along the expulsion direction (E) nearingly to the container (2).

In a 42nd aspect according to any one of aspects from 38 to 41, the passage seating (8) of the coupling element (4) extends substantially parallel to the expulsion direction (E); during the step of dispensing the passage seating (8) enables passage of the axial intersection portion (14) of the activating element (5) and the sliding thereof nearingly to the container (2).

In a 43rd aspect according to any one of aspects from 39 to 42, the second engaging portion (11) of the coupling element (4) comprises at least a lateral wall (18) extending substantially parallel to the expulsion direction (E), the radial intersection portion (16) of the coupling element (4) emerging radially from the lateral wall (18) towards the internal lateral wall (5b) of the housing compartment (5a), and wherein the support portion (17) of the coupling element (4) is defined by at least a portion of free end surface of the lateral wall (18) located on the opposite side with respect to the first engaging portion (10) of the coupling element (4), and wherein the projection (12) of the activating element (5) comprises at least a ribbing (19) emerging from the internal lateral wall (5b) of the housing compartment (5a), the ribbing (19) defining the radial intersection portion and the support portion (15) of the activating element (5), and wherein during step of elastic deformation the ribbing, when distancing from the lateral wall (18) of the coupling element (4) and being able to rotate relatively thereto about the expulsion axis (E), and wherein, during the dispensing step, the ribbing runs internally of the passage seating (8) of the coupling element (4).

In a 44th aspect according to any one of aspects from 33 to 43, the dispensing step includes emission of a predetermined quantity of cryogenic substance (C) that is lower than the total cryogenic substance (C) present internally of the container (2).

In a 45th aspect according to the preceding aspect, the container (2) comprises a general chamber (2c) configured so as to contain a predetermined quantity of cryogenic substance (C), the container (2) further comprising a pre-chamber (2d) exhibiting at least an inlet (22) set the general chamber (2c) in fluid communication with the pre-chamber (2d), the pre-chamber (2d) further exhibiting at least an outlet (23) for setting the pre-chamber (2d) in fluid communication with the opening (2a) of the container (2), the container (2) comprising at least a valve (24) operatively active on the inlet (22) and on the outlet (23) of the pre-chamber (2d); during the dispensing step the pre-chamber (2d) is in fluid communication with the opening (2a) of the container while fluid communication between the general chamber (2c) and the inlet (22) of the pre-chamber (2d) is inhibited; during the dispensing step only the predetermined quantity of cryogenic substance (C) being able to exit from the outlet (23) of the pre-chamber (2d), and wherein the valve (24), during the safety step and/or in the intermediate condition, places the pre-chamber (2d) in fluid communication with the general chamber (2c) while it prevents passage of fluid between the pre-chamber (2d) and the opening (2a) of the container (2).

In a 46th aspect according to the preceding aspect the pre-chamber (2d) exhibits a smaller volume with respect to the volume of the general chamber (2c), and wherein the ratio between the volume of the general chamber (2c) and the volume of the pre-chamber (2d) is greater than 2, in particular greater than 3, still more in particular greater than 4.

In a 47th aspect according to any one of aspects from 33 to 46, the method comprises a step of predisposing at least an applicator (25) in fluid communication with the dispensing conduit (6) of the activating element (5), the activating element (5) being configured such as to guide the emission of the cryogenic substance (C), the dispensing step including a sub-step of directing the cryogenic substance (C) via the applicator (25).

In a 48th aspect according to the preceding aspect the applicator (25) exhibits a body (26) extending along a prevalent development direction between a first and a second end (27, 28), the applicator (25) being engaged, at the first end (27), to the activating element (5) and emerging from an external wall (5c) thereof in an outgoing direction with respect to the housing compartment (5a) of the activating element (5), and wherein the applicator (25) exhibits a through-opening (29) extending along of all the body (26) from the first end (27) to the second end (28), the dispensing conduit (6) of the activating element (5) being in fluid communication with the opening (29) of the applicator (25), the applicator (25) being configured such as to distance the dispensing conduit (6) from an application zone (P) of the cryogenic substance (C), and wherein the method comprises a step of interposing the applicator (25) between the activating element (5) and the application zone (P) in such a way as to maintain the activating element (5) and the application zone (P) at a predetermined distance, in particular maintaining the development direction of the body (26) of the applicator (25) substantially perpendicular with respect to the part to be treated, at least during the dispensing step, so that a symmetrical and homogeneous freezing is obtained.

BRIEF DESCRIPTION OF THE DRAWINGS

Some embodiments and aspects of the invention will be described in the following with reference to the appended drawings, provided only by way of non-limiting example, in which.

DETAILED DESCRIPTION

Figure 1:
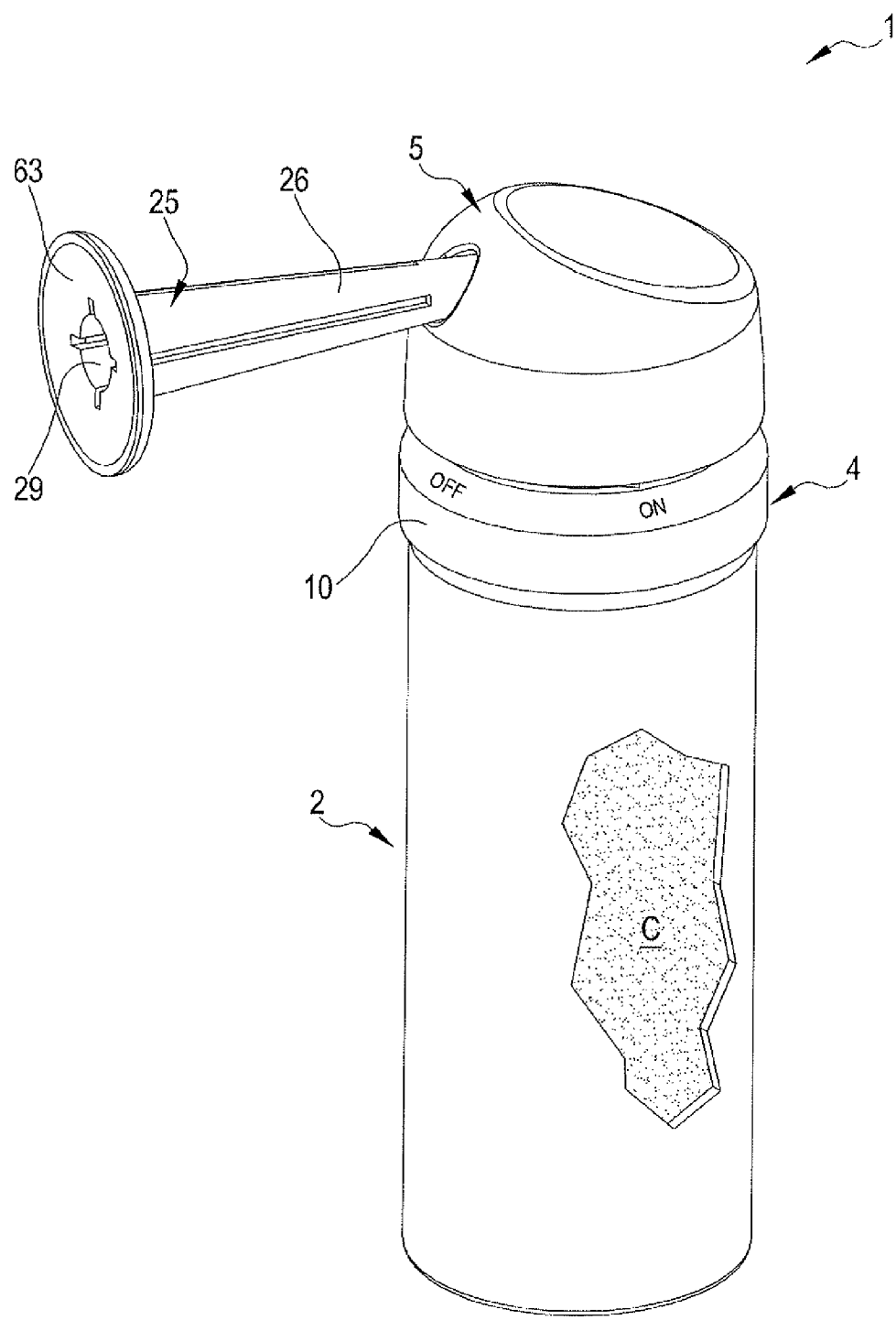
FIG. 1 is a perspective view of a dispenser of cryogenic substances in accordance with the present invention.

Dispenser of Cryogenic Substances 1 denotes in its entirety a dispenser of cryogenic substances C in particular used for topical treatment of tissues.

Cryogenics are often used in dermatology for treatment of various pathologies and/or malformations of the skin, caused by aging and other reasons, for example for treatment of verrucas, seborrheic keratosis, skin tags, freckles, cutaneous formations, unaesthetic skin conditions, etc.

The advantages in the use of cryogenics for pathologies/blemishes mentioned above are linked to the possibility of operating without medical assistance and, consequently, without the need for anaesthetics, to prevent the appearance of scars, obviate the use of dressings and to reduce the convalescent period post-treatment.

A cryogenic substance C is taken to mean a substance having a very low boiling temperature, in particular lower than −73° C.; some of the more common cryogenic substances are: dimethyl ether, nitrogen, argon, $CO_2$, oxygen and ammonia. The dispenser 1 of the present invention is configured to operate with a dimethyl ether-based mixture, though other cryogenic substances C could also be used.

These substances are maintained under pressure and in the liquid state internally of an appropriate can. As can be seen in the figures, the dispenser 1 comprises a container (2) configured such as to contain a predetermined quantity of cryogenic substance (C). In the appended figures, a preferred but not exclusive embodiment of the container 2 is illustrated, which exhibits a substantially cylindrical shape. The container 2 is substantially a recipient defining internally thereof a housing chamber or compartment 2c, in fluid communication with the outside environment by means of at least an opening 2a. In a preferred embodiment, illustrated in the figures, the container 2 is provided with one and one only opening 2a in communication with the outside environment.

Figure 2:
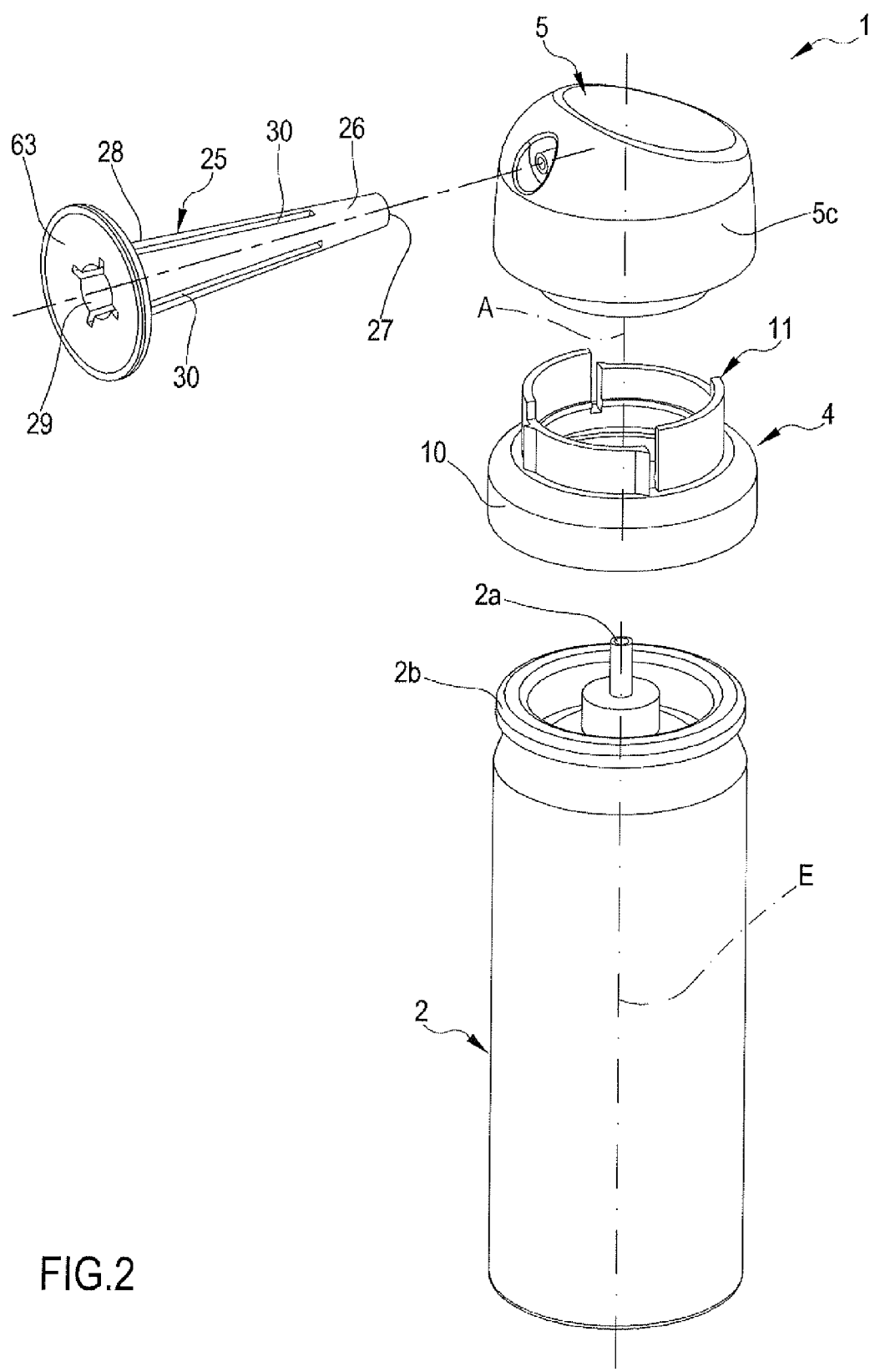
FIG. 2 is an exploded view of the dispenser of cryogenic substances of FIG. 1.

The opening 2a is arranged, non-limitingly, at an upper base of the cylinder: the opening 2a enables exit of the cryogenic substance C along an expulsion direction E (see FIG. 2).

The container 2 comprises a valve 3 active on the opening 2a and configured so as to be arranged in a normally closed condition in which it prevents exit of the cryogenic substance C of the opening 2a. The valve 3 is further configured to be arranged, following an activating operation thereof, in a passage condition in which the valve 3 enables outlet of the cryogenic substance C.

In fact, the valve 3 is a normally-closed valve which in the standard condition prevents the cryogenic substance C from exiting from the container 2. The activating of the valve 3 enables setting the chamber 2c of the container 2 in fluid communication with the outside environment.

As previously mentioned, the cryogenic substance C present in the container 2 is pressurized and in the liquid state: the pressure of the cryogenic substance C, following activation of the valve 3, enables the substance C to be expelled from the opening 2a in the form of gas, or, alternatively, is nebulized (aerosol).

In the most common form the container 2 is in fact a spray can containing the cryogenic substance C in the liquid state.

Figure 9A:
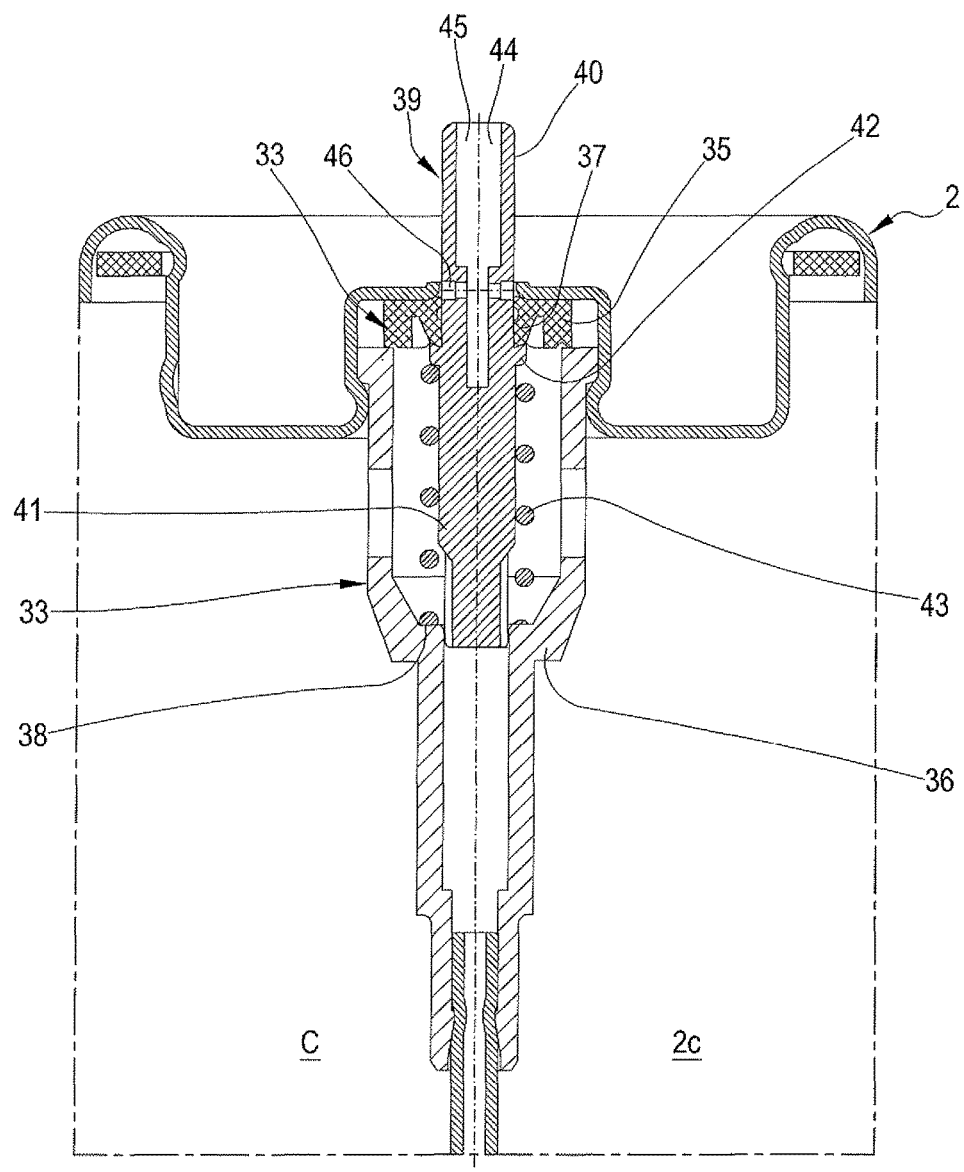
FIGS. 9A and 9B are views in detail of a container of said dispenser according to a first embodiment.
Figure 9B:
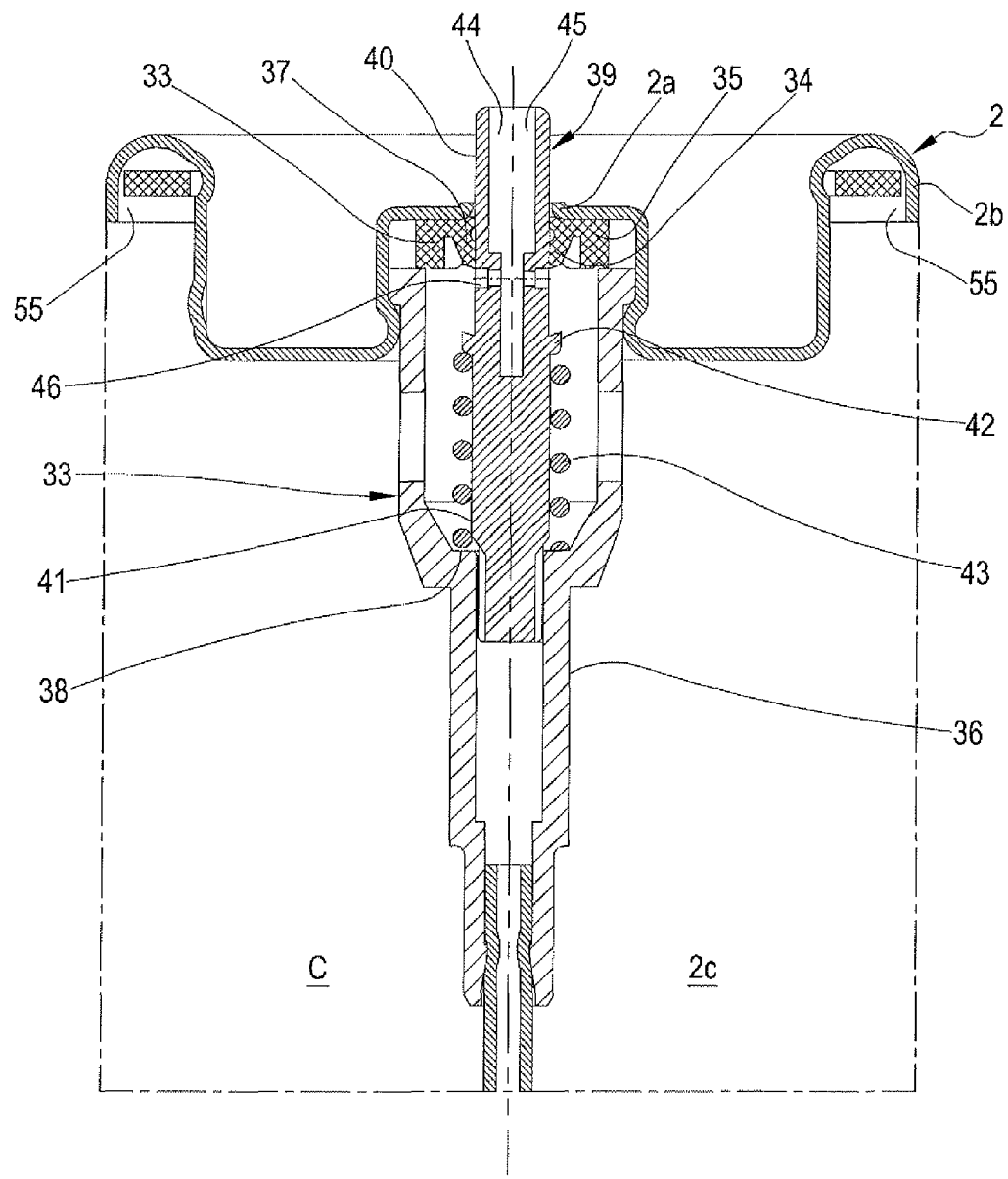
Figure 9C:
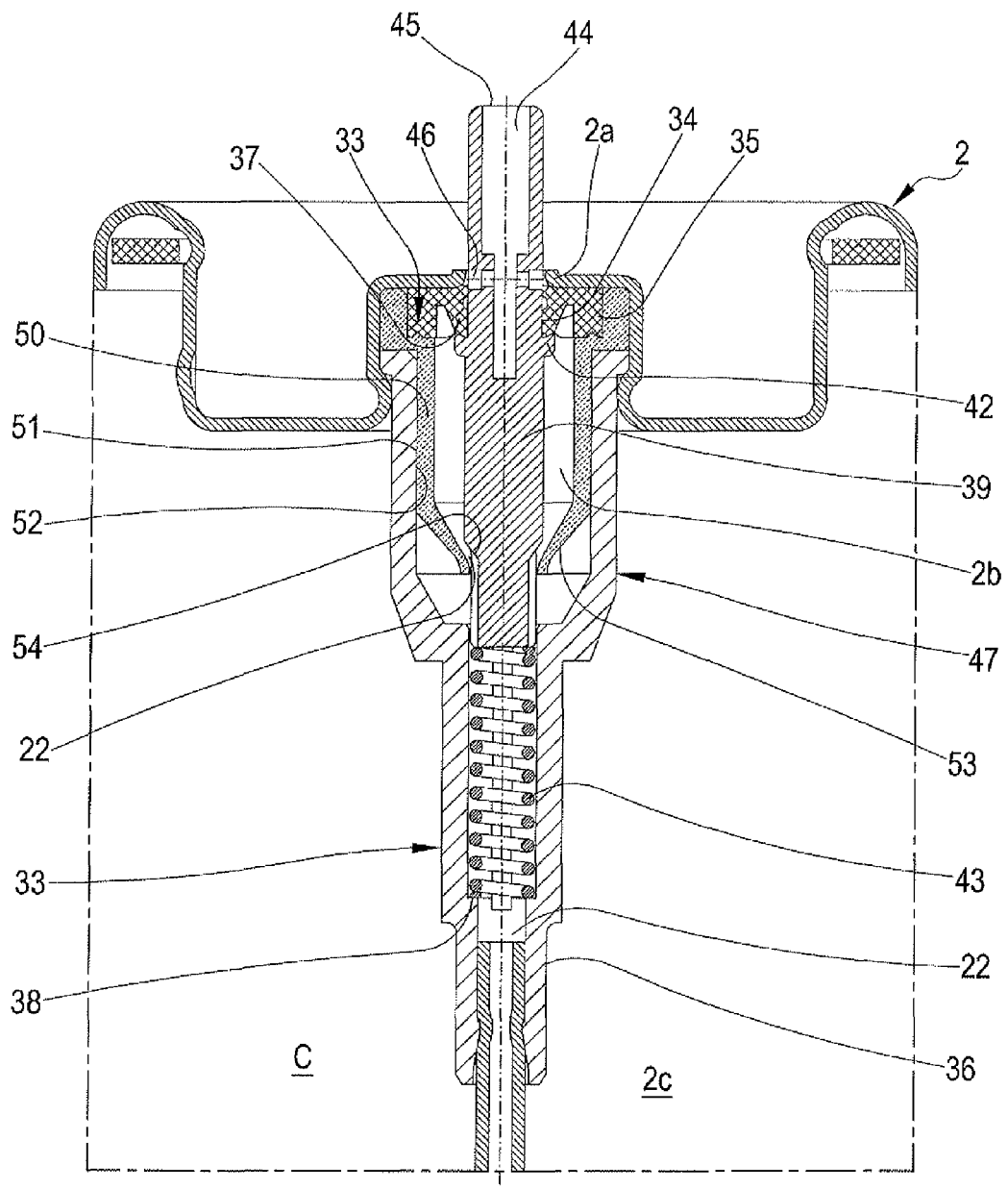
FIGS. 9C and 9D are views in detail of a container of said dispenser according to a second embodiment.
Figure 9D:
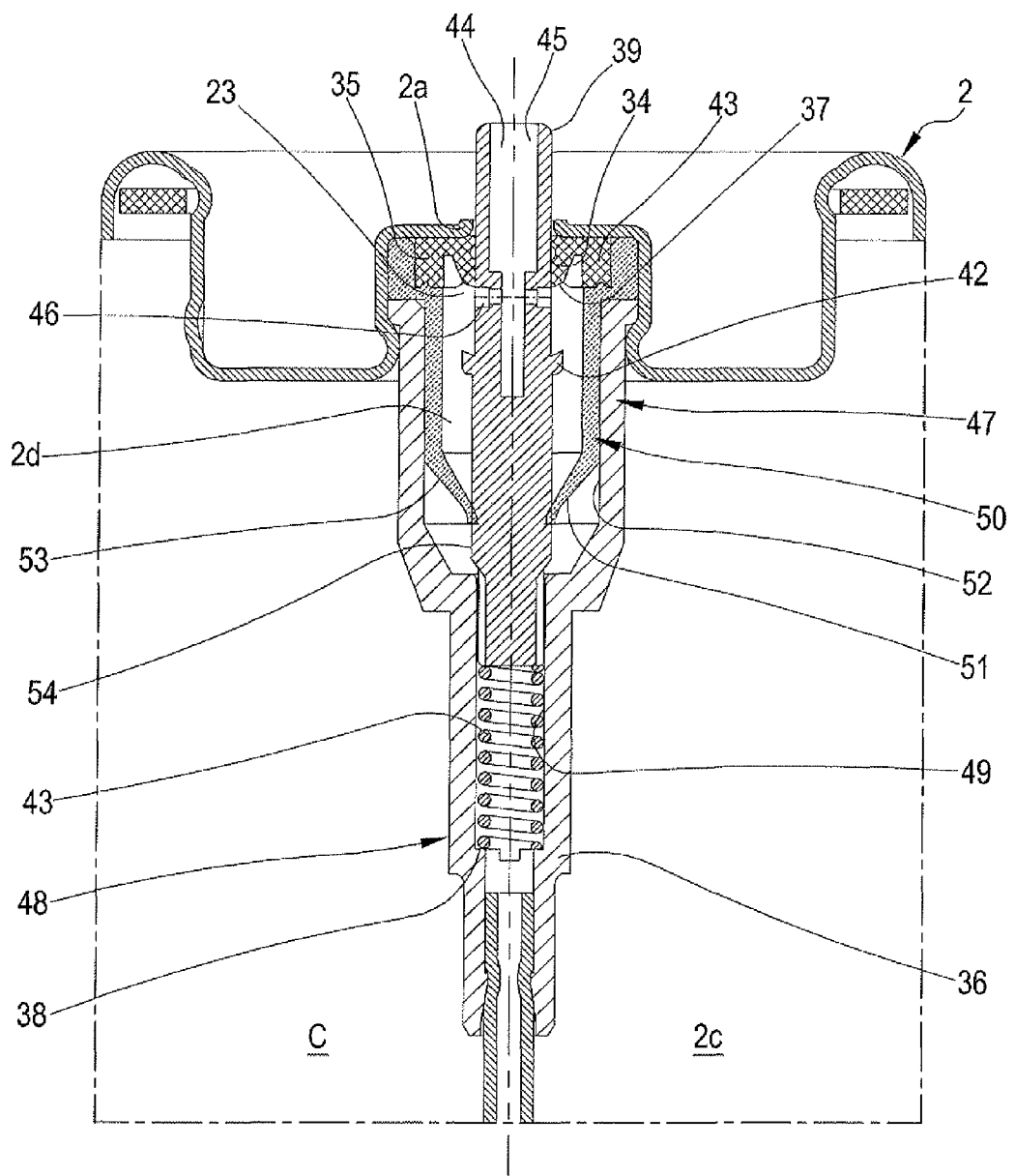

In figures from 9A to 9D, and non-limitingly, two different embodiments are illustrated of the valve 3 mountable at the opening 2a of the container 2; in particular, in FIGS. 9A and 9B, a first embodiment of the valve 3 is illustrated, while FIGS. 9C and 9D show a second embodiment of the valve 3.

In the first embodiment illustrated in FIGS. 9A and 9B, the valve 3 comprises a constraining element 33 fixed solidly to inside the chamber 2c of the container 2, at the opening 2a. The element 33 exhibits an opening 34 located at the opening 2a and in fluid communication therewith. In particular, as is visible in FIG. 9B, the opening 34 of the constraining element 33 is aligned with the opening 2a and is consecutively arranged with respect thereto; in this way the opening 34 of the constraining element 33 defines with the opening 2a a single passage able to set in fluid communication the general chamber 2c of the container 2 with the external environment. The constraining element 33 extends internally of the housing chamber 2c of the container between a first and a second end 35, 36 at which the constraining element 33 comprises a first and a second axial abutment 37, 38.

The valve 3 further comprises a body 39 extending along a prevalent development direction and engaged internally of the opening 34 of the valve 3. The prevalent development direction of the body 39 is substantially parallel to the expulsion direction E (see FIG. 9B) and is mobile by sliding internally of the openings 34 and 2b (as previously described, defining a single passage) substantially along the expulsion direction.

In greater detail, the body 39 comprises a first portion 40 emerging from the container 2 and a second portion 41 located internally of the housing compartment 2c of the container 2. The second portion 41 comprises an abutment 42, able to abut the first axial abutment 37 of the constraining element 33 in the normally closed condition of the valve 3: the first axial abutment 37 of the constraining element 33 substantially defines an endrun point of the body 39 so as to prevent it from exiting from the general chamber 2c of the container 2 (see the condition of the valve of FIG. 9A).

As visible in FIGS. 9A and 9B, an elastic element 43 is engaged between the abutment 42 of the body 39 and the second axial abutment 38 of the constraining element 33, which elastic element 43 is configured so as to force contact between the abutment 42 of the body 39 and the first abutment 37 of the first constraining element 33.

The first portion 40 of the body 39 is configured so as to receive an opening force directed along the expulsion direction E and having an entering direction with respect to the container 2; by applying on the first portion 40 of the body 39 an opening force greater than the resistant force provided by the elastic element 43 it is possible to slide the body 39 along a sliding direction S that is substantially parallel to the expulsion direction E of the cryogenic substance.

As can be seen in FIGS. 9A and 9B, the body 39 comprises an outlet line 44 exhibiting a first opening 45 located at the first portion 40 and which is in fluid communication with a second opening 46 positioned on a lateral wall of the body 39. The second opening 46 is positioned in such a way as to prevent fluid communication between the housing chamber 2c of the container 2 and the external environment when the valve 3 is arranged in the normally-closed condition: in this condition the abutment 42 of the body 39 is abutted on the first abutment 37 of the constraining element 33 (the starting condition of the valve maintained by the elastic element 42 and visible in FIG. 9A).

In the preferred embodiment illustrated in FIG. 9A, the second opening 46, in the normally closed condition of the valve 3, is arranged externally of the housing chamber 2c of the container 2, and in particular is aligned to the opening 2a of the container 2.

Following the translation of the body 39 along the sliding direction S (a condition defined following the application, on the body 39, of an opening force that is greater than the resistant force provided by the elastic element 43), the second opening 46 can be arranged internally of the housing chamber or general chamber 2c of the container 2 and place in fluid communication the internal volume of the container 2 with the external environment (passage condition of the valve 3 illustrated in FIG. 9B).

In this condition the second portion 41 occludes the fluid passage from the lower zone of the chamber towards the exit in such a way that only a predetermined quantity of cryogenic fluid (in particular the fluid contained in the same chamber which contains the elastic element) can be dispensed with the single activation.

In the second embodiment illustrated in FIGS. 9C and 9D, the valve 3 also comprises a constraining element 33 solidly fixed to the inside of the container 2, at the opening 2a. The element 33 exhibits an opening 34 located at the opening 2a and in fluid communication therewith. In particular, as can be seen in FIG. 9C, the opening 34 of the constraining element 33 is aligned with the opening 2a and consecutively arranged with respect thereto: in this way the opening 34 of the constraining element 33 defines, with the opening 2a, a single passage placing the container 2 in fluid communication with the outside environment. The constraining element 33 extends internally of the container 2 between a first and a second end 35, 36 at which the constraining element 33 comprises a first and a second axial abutment 37, 38.

The constraining element 33 illustrated for example in FIG. 9C (second embodiment) comprises a batching device 47 defining, internally of the general chamber 2c of the container 2, a pre-chamber 2d, in particular, interposed between the opening 2a of the container 2 and the general chamber 2c thereof.

In greater detail, the batching device 47 emerges distancingly from the opening 2a of the container 2 along a prevalent development direction between the first and a second end 35, 36 of the constraining element 33.

At the second end 36, the batching device 47 comprises, non-limitingly, an inlet 22 for setting the general chamber 2c in fluid communication with the pre-chamber 2d. At the first end 35, the device 47 exhibits at least an outlet 23 able to place the pre-chamber 2d in fluid communication with the opening 2a of the container 2.

In structural terms, it can be seen that the batching device 47 exhibits, non-limitingly, a form of cylindrical symmetry about the expulsion direction E of the cryogenic substance C.

As visible in FIG. 9B, the device 47 comprises a support portion 48 at the second end 36 of the device 47. The support portion 48 exhibits a housing seating 49 able to at least partially contain an elastic element 43, in particular a spring. The second axial abutment 38 of the constraining element 33 on which the elastic element 43 rests is defined at the base of the housing seating 49.

In fact, the elastic element 43 rests, on a side, on the second axial abutment 38 while, on the opposite side, it is configured to abut on an end portion of the body 39 as will be better explained in the following.

In the preferred embodiment illustrated in FIG. 9C, the inlet 22 of the pre-chamber 2d is arranged, non-limitingly, at the base of the housing seating 49. Alternatively, the inlet 22 can be arranged at least at a lateral wall of the batching device 47 (a condition not illustrated in the figures).

As visible in FIGS. 9C and 9B, the batching device 47 further comprises a closing portion 50, configured to abut the body 39 so as to define the pre-chamber 2d. In particular, the closing portion 50 comprises at least a tab 51 emerging from a lateral wall 52 of the device 47 nearingly to the body 39. The tab 51 terminates with an end portion 53 complementarily-shaped to a portion of the body 39.

In the second embodiment (FIGS. 9C and 9D), the valve 3 also comprises a body 39 extending along a prevalent development direction and engaged internally of the opening 34 of the valve 3. The prevalent development direction of the body 39 is substantially aligned to the expulsion direction 34 and 2b (as previously described defining a single passage) substantially along the expulsion direction E.

In greater detail, the body 39 comprises a first portion 40 emerging from the container 2 and a second portion 41 located internally of the pre-chamber 2d of the container 2. Differently to the first embodiment, the second portion 41 of the body 39 is located directly internally of the pre-chamber 2d which is contained internally of the general chamber 2c.

The second portion 41 comprises an abutment 42, able to abut the first axial abutment 37 of the constraining element 33: the first axial abutment 37 of the constraining element 33 substantially defines an endrun point of the body 39 for preventing the body 39 from exiting from the container 2 (condition of FIG. 9C).

The body 39 further comprises a further abutment 42*a* opposite the abutment 42 with respect to the body 39. In fact, the further abutment 42*a* is arranged on a terminal portion of the body 39 distanced from the opening 2*a* of the container 2. The abutment 42*a* is able to contact the elastic element 43. As visible for example from FIG. 9C, the elastic element 43 is interposed between the further axial abutment 42*a* of the body 39 and the second axial abutment 38 of the constraining element 33. The elastic element 43 is configured so as to force contact between the abutment 42 of the body 39 and the first abutment 37 of the first constraining element 33 and maintain it in the normally-closed condition.

As with the first embodiment, the first portion 40 of the body 39 is configured so as to receive an opening force directed along the expulsion direction E and having an entering direction with respect to the container 2; by applying on the first portion 40 of the body 39 an opening force greater than the resistance force offered by the elastic element 43 it is possible to slide the body 39 along a sliding direction S substantially parallel to the expulsion direction E of the cryogenic substance C (FIG. 9D).

In the second embodiment illustrated in FIGS. 9C and 9D, the body 39 further comprises an abutment 54 able to abut on the end portion 53 of the tab 51 following the translation of the body 39 internally of the container 2.

In fact, in the endrun condition of the body 39, i.e. in the condition in which the first abutment 37 of the constraining element 33 is in contact with the abutment 42 of the body 39, the abutment 54 is distanced from the end portion 53 (FIG. 9C). While, following the translation of the body 39 (translation of the body along the sliding direction S) internally of the container 2, the endrun 54 abuts on the end portion 53 (FIG. 9D).

As with the first embodiment, the body 39 of FIG. 9C-9D comprises an outlet line 44 exhibiting a first opening 45 located at the first portion 40 and which is in fluid communication with a second opening 46 located on a lateral wall of the body 39. The second opening 46 is positioned such as to prevent fluid communication between the container 2 and the external environment when the valve 3 is arranged in the normally-closed configuration: in this condition the abutment 42 of the body 39 is abutted to the first abutment 37 of the constraining element 33 (starting condition of the valve illustrated in FIG. 9C). In the preferred embodiment illustrated in FIG. 9C, the second opening 46, in the normally closed condition of the valve 3, is arranged externally of the housing chamber 2*c* of the container 2, in particular it is aligned to the opening 2*a* of the container 2.

Following the translation of the body 39 along the sliding direction S (a condition defined following the application on the body 39 of an opening force greater than the resistant force offered by the elastic element 43), the second opening 46 can be arranged internally of the container 2, in particular internally of the pre-chamber 2*d*, and can set the pre-chamber 2*d* in fluid communication with the external environment (FIG. 9D).

In detail, in the second embodiment, the movement of the body 39 internally of the container 2 enables the abutment 54 of the body 39 to abut on the end portion 53 of the tab 51: in this way the body 39, in particular the abutment 54, obstructs the inlet 22 of the pre-chamber 2*d* in such a way as to prevent passage of fluid between the pre-chamber 2*d* and the general chamber 2*c*.

In fact, also in the second embodiment illustrated in FIGS. 9C-9D, only the predetermined quantity of cryogenic substance C arranged internally of the pre-chamber 2*d* can exit from the container 2 during the passage condition of the valve 3.

In the closed condition of the valve 3, the fluid communication between the general chamber 2*c* and the pre-chamber 2*d* enables injecting into the pre-chamber 2*d* further cryogenic substances C to be dispensed during a subsequent passage condition of the valve.

It is useful to note that in both the embodiments, independently of how long the valve 3 of the dispenser 1 is maintained in the passage condition, only the predetermined quantity of cryogenic substance C contained in the pre-chamber 2*d* can be dispensed through the opening 2*a* of the container 2.

Continuing with the description of the container 2, it is possible to observe that the container further comprises an engaging portion 2*b* located at the opening 2*a*. The engaging portion 2*b* can define at least an undercut with respect to the expulsion direction E of the cryogenic substance C. in the preferred embodiment, for example visible in FIG. 3, the engaging portion 2*b* of the container 2 comprises a fold 55 exhibiting, non-limitingly, a circular development defining a closed profile.

The dispenser 1 further comprises a coupling element 4 constrained stably to the container 2 substantially at the opening 2*a*. In particular the coupling element 4 comprises a first engaging portion 10 constrained to the engaging portion 2*b* of the container 2.

In greater detail, the first engaging portion 10 of the coupling element 4 is able to abut in undercut on the engaging portion 2*b* of the container 2: in this way the container axially constrains the coupling element 4 so as to prevent it from translating along the expulsion direction E.

Figure 3:
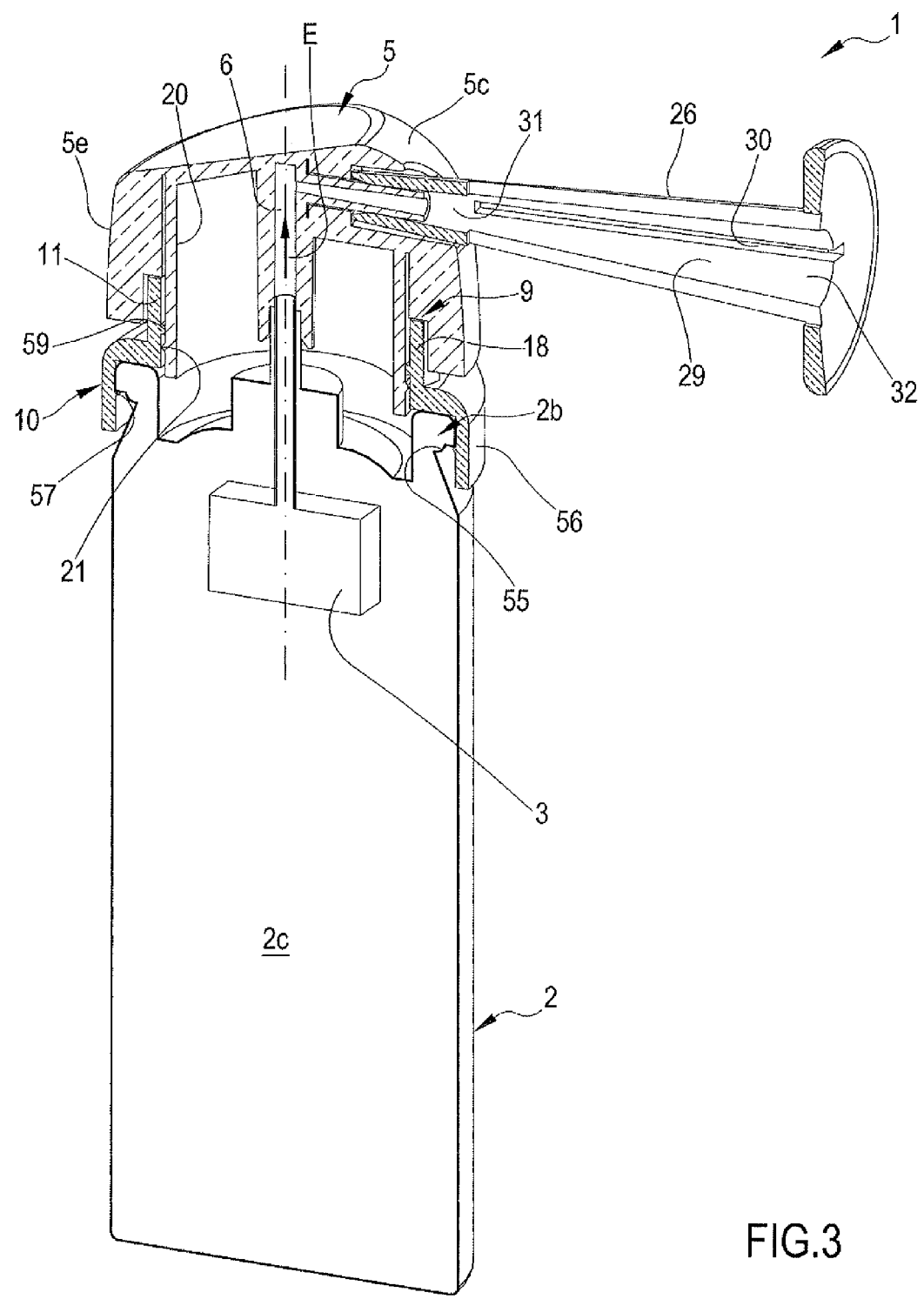
FIG. 3 is a schematic section view, along a longitudinal plane, of the dispenser of FIGS. 1 and 2.

As is visible for example in FIG. 3, the first engaging portion 10 of the coupling element 4 comprises, in a non-limiting way, a seal element 56 at least partly complementarily-shaped to the engaging portion 2*b* of the container 2. This seal element 56 exhibits at least a projection 57 able to abut the undercut of the engaging portion 2*b*. In the preferred embodiment, illustrated for example in FIGS. 10 and 11, the seal element 56 is entirely complementarily shaped to the engaging portion 2*b* of the container, in particular defining a lateral wall having, in a transversal section, a circular profile; the projection 57 emerges from the lateral wall nearingly to the undercut of the element of the container 2.

As visible for example from the section view of FIG. 3, the first engaging portion 10 further comprises an abutting element 58 connected to the seal element 56, in particular joined in a single piece therewith, able to rest on the engaging portion 2*b* of the container 2. In particular, the seal element 56 and the abutting element 58 define a substantially L-shaped profile entirely in contact with the engaging portion 2*b*: the engaging portion 2*b* is substantially interposed between the projection 57 and the abutting element 58 of the coupling element 4.

The coupling element 4 further comprises a second engaging portion 11 emerge from the first engaging portion 10 distancingly with respect thereto, in particular, parallel to the expulsion direction E of the cryogenic substance C.

In greater detail, the second engaging portion 11 of the coupling element 4 exhibits a lateral wall 18 extending substantially parallel to the expulsion direction E. The lateral wall 18 exhibits, in a non-limiting way, a hollow cylindrical shape developing about an axis A parallel to the expulsion direction E and having a smaller radial dimension with respect to the radial dimension of the seal element 56.

Figure 3A:
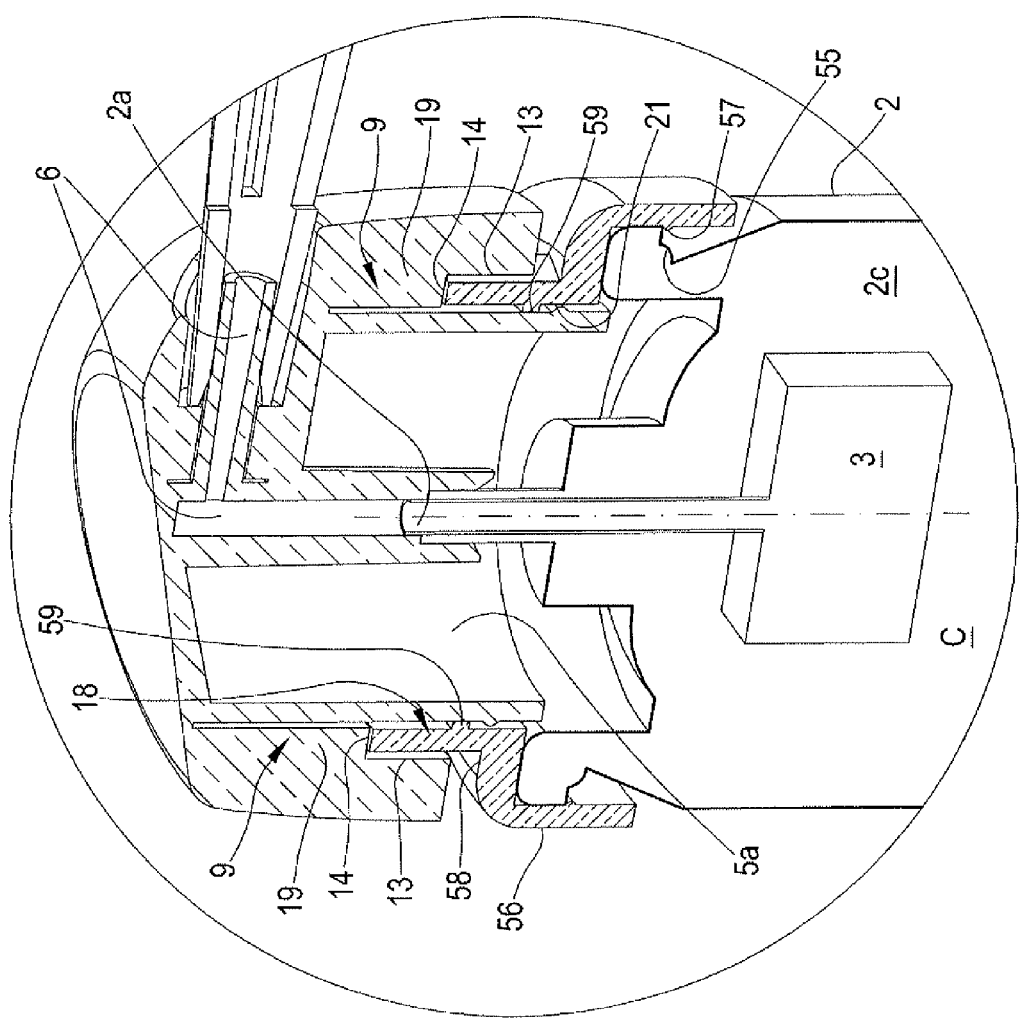
FIG. 3A is a detail of FIG. 3.

The lateral wall 18 is non-limitingly joined in a single piece with the abutting element 58; in a longitudinal section, the abutting element 58 and the lateral wall 18 define a substantially L-shaped profile (see the section view of FIG. 3 and the detailed view of FIG. 3A).

The second portion 11 of the coupling element 4 is configured so as to engage and cooperate with an activating element 5 which will be more fully described in the following.

In particular, the second engaging portion 11 comprises a further projection 59 arranged internally of the lateral wall 18 and configured so as to engage the activating element 5. As visible in the detail of FIGS. 10 and 11, the projection 59 extends over all the lateral wall 18 such as to form a circular profile along a transversal plane, in particular perpendicular, to the axis A of the coupling element 4.

As visible from the figures, the second engaging portion 11 of the coupling element 4 further comprises at least a blocking portion 7. The blocking portion 7 is, non-limitingly, arranged on the lateral wall 18 and emerges with respect to a lateral external surface thereof, for example in the form of a tooth provided with an inclined wall connected to the lateral wall 18 which terminates with a perpendicular surface to the lateral wall.

Figure 11:
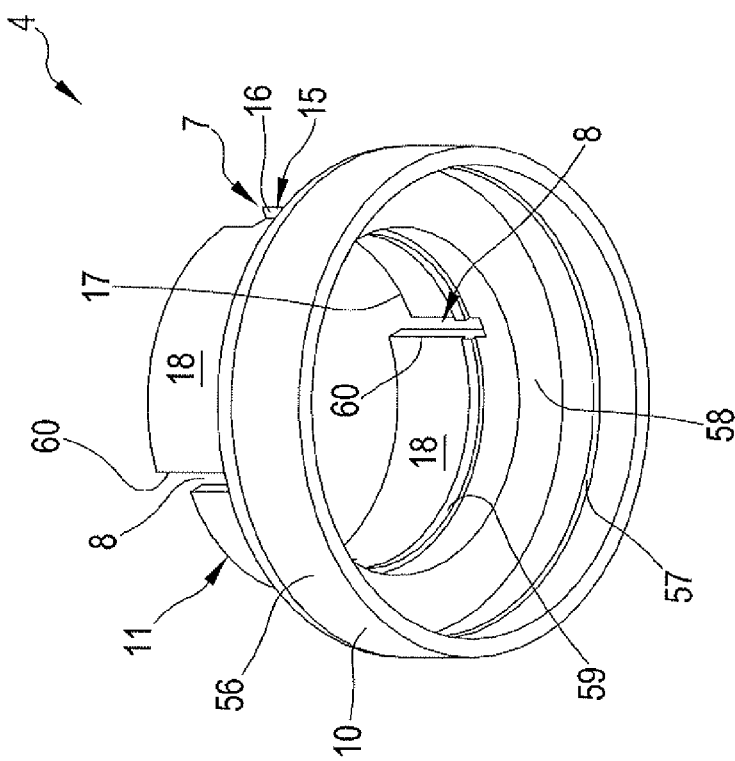
FIGS. 10 and 11 are perspective views of a coupling element of the dispenser of cryogenic substances.
Figure 10:
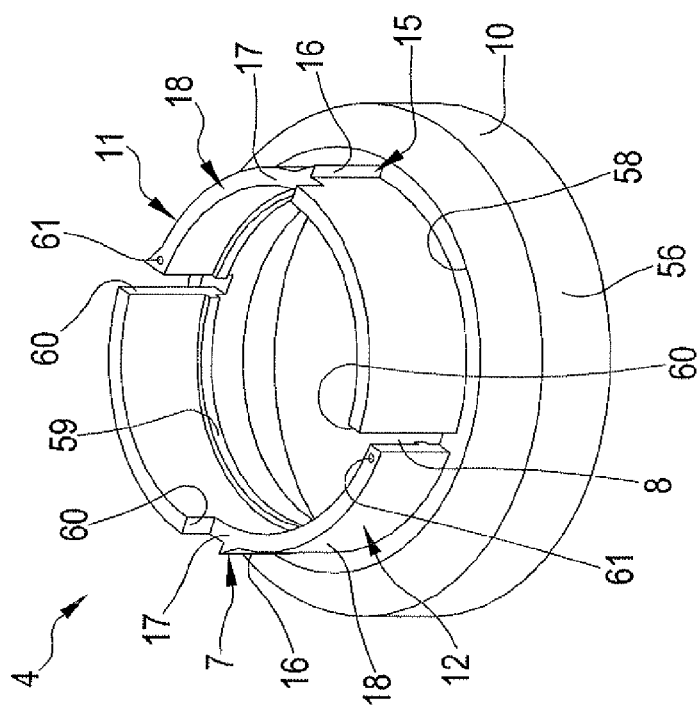
Figure 13:
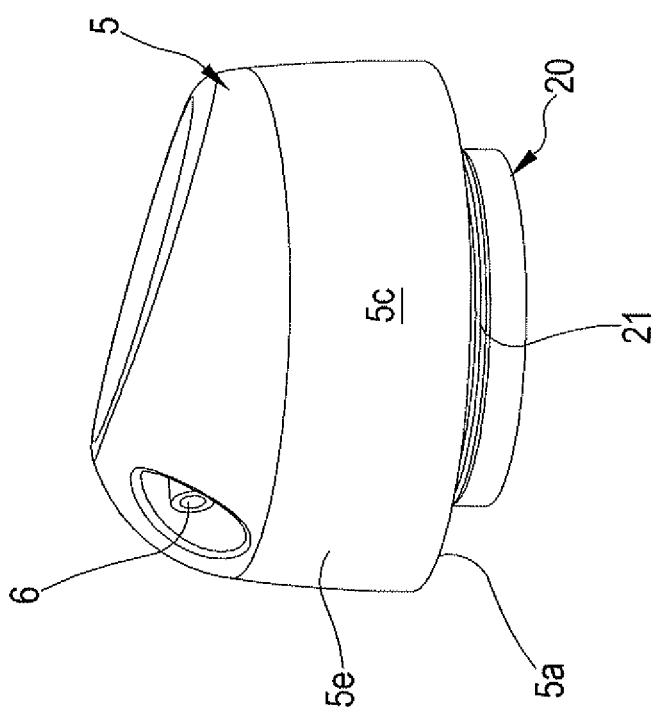
FIGS. 12 and 13 are perspective views of an activating element of the dispenser of cryogenic substances.

In other terms the blocking portion 7 exhibits at least a projection 15 defining a radial intersection portion 16 and a support portion 17 (see FIGS. 10 and 11).

The radial intersection portion 16 defines a radial undercut emerging from the external lateral surface of the wall 18. The support portion 17 is instead able to substantially define an axial blocking portion along the expulsion direction E of the cryogenic substance C (as will be more fully described in the following).

The figures represent a preferred embodiment of the radial intersection portion 16 which develops, non-limitingly, over all the height-extension of the wall 18 along the axis A (parallel to the expulsion direction E). The radial intersection portion 16 exhibits, according to a transversal section, a substantially triangular profile (with a tooth).

In the figures a preferred embodiment is illustrated in which the coupling element 4 exhibits two blocking portions 7, angularly offset (more precisely, opposite) with respect to one another in relation to the axis A of the coupling element 4.

In an alternative realisation, not illustrated in the accompanying figures, there can be a number of blocking portions that is greater than 2 or even one only blocking portion.

As visible for example from the detail of FIGS. 10 and 11, the second engaging portion 11 of the coupling element 4 further comprises at least a passage seating 8. The seating is non-limitingly arranged at the lateral wall 18 and extends substantially over the whole axial development thereof, parallel to the axis A of the coupling element 4.

The passage seating 8 defines, non-limitingly, a through-seating crossing the lateral wall 18 (or, in other terms, an interruption of the lateral wall 18) which defines a straight line parallel to the axis A (parallel to the expulsion direction E of the cryogenic substance C).

The passage seating 8 is angularly offset with respect to the blocking portion 7 in relation to the expulsion direction E, in particular with respect to the axis A of the coupling element 4. In the preferred embodiment, there is non-limitingly a number of passage seatings 8 equal to the number of blocking portions 7. In particular, a configuration of the dispenser 1 is illustrated that exhibits, non-limitingly, two blocking portions 7 and two respective passage seatings 8.

As visible for example in FIGS. 10 and 11, the passage seating 8 is optionally offset angularly by 90° with respect to the blocking portion 7. As can be seen in FIGS. 10 and 11, the lateral wall 18 can further comprise a radial endrun portion 60 circumferentially distanced with respect to each blocking portion 7 and to each passage seating 8. Further, the lateral wall 18 can comprise an axial projection 61 (see FIG. 10) emerging from an upper surface of the wall 18. The axial projection 61 is preferably arranged at the passage seating 8 so that the seating is interposed between the radial endrun 60 and the axial projection 61 (see FIG. 10).

Alternatively the axial projection 61 could be replaced by a small relief (such a tooth projecting less than the tooth 15 and with opposite inclined surface, not shown in the figures) positioned at the lateral wall 18 and with the aim of providing a tactile and/or acoustic indication of the reaching of position of an activating element. The structure and function of the endrun 60 and the projection 61 will be more fully described in the following.

As previously mentioned, the dispenser 1 further comprises an activating element 5 engaged to the coupling element 4. In greater detail, the activating element 5 is engaged to the second engaging portion 11 of the coupling element 4 so that the coupling element 4 is interposed between the container 2 and the activating element 5.

In structural terms, the activating element 5 comprises a body 5c defining internally thereof a housing compartment 5a: in the engaging condition between the activating element 5 and the coupling element 4, the second portion 11 thereof is at least partly arranged internally of the housing compartment 5a.

Figure 12:
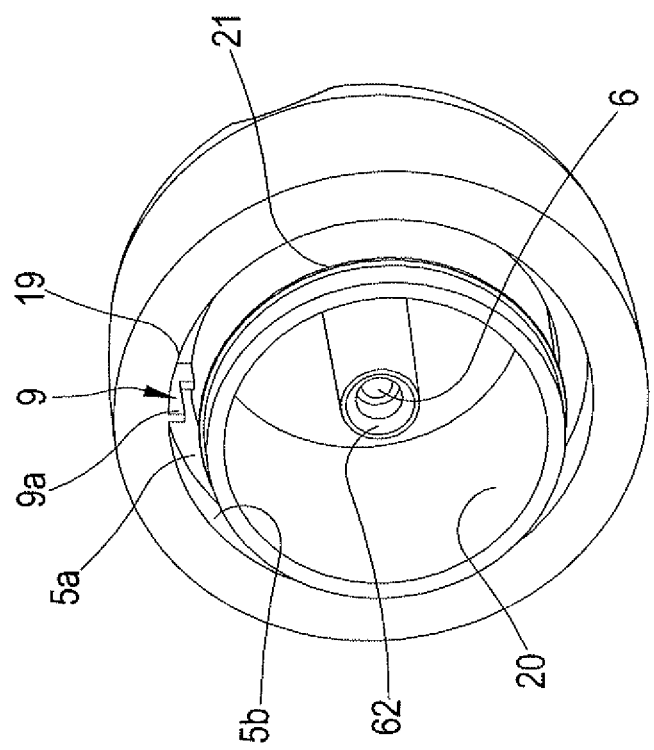

As visible in FIG. 12, internally of the housing compartment 5a of the activating element 5 there is an engaging portion 20 able to abut to the second engaging portion 11 of the coupling element 4. The engaging portion 20 emerges from the internal wall of the housing compartment 5a parallel to the expulsion direction E of the cryogenic substance C (consequently parallel to the axis A of the coupling element 4) in order to insert in the lateral wall 18 of the coupling element 4). The engaging portion 20 exhibits, non-limitingly, a hollow cylindrical shape complementarily-shaped to the lateral wall 18 of the coupling element 4. In order to enable the constraint between the coupling element 4 and the activating element 5, the activating element exhibits an abutment 21 able to abut the further projection 59 arranged internally of the lateral wall 18: in this condition the further projection 59 of the lateral wall 18 defines an axial undercut for the abutment 21 which can stably constrain the activating element 5 to the blocking element (substantially preventing translation of the activating element distancingly with respect to the container 2.)

The engaging portion 20 of the activating element 5 further enables centring thereof on the coupling element as well as guiding thereof during the relative movement (see also the section of FIG. 3).

A dispensing conduit 6 is present internally of the engaging portion 20 of the activating element 5, which dispensing conduit 6, in the engaged condition between the coupling element 4 and the activating element 5, is in fluid communication with the opening 2a of the container 2; this conduit 6 is configured so as to guide the emission of the cryogenic substance C towards the external environment.

In greater detail, the dispensing conduit 6 exhibits an abutting portion 62 (visible in FIG. 12) in contact with the first portion 40 of the body 39 emerging from the container 2; the outlet line 44 of the body 39 is in fluid communication with the dispensing conduit 6. During the passage condition of the valve 3, the cryogenic substance C is able to exit from the line 44, enter the dispensing conduit 6 and then exit from the activating element 5.

As is visible from the section view of FIG. 3, and the detail of FIG. 3A, the activating element 5 further comprises an active portion 9 which cooperates with the blocking portion 7 and the passage seating 8 of the coupling element 4.

In particular, the activating element 5 is configured so as to define, in cooperation with the coupling element 4, at least a dispensing condition in which the active portion 9 of the activating element 5 is at and cooperates with the passage seating 8; in particular in the dispensing condition the active portion is translatable in the seating 8 along a sliding direction S nearingly to the container 2.

Following the activation along the expulsion direction towards the container 2, the activating element 5 is configured so as to arrange the valve 3 in the passage condition and consequently enable the exiting of at least a part of the cryogenic substance C from the opening 2a.

The activating element 5 is further configured to define, in cooperation with the coupling element 4, at least a safety condition.

The safety condition is attained by relative rotation (by about 90°) of the activating element 5 with respect to the coupling element 4.

In the safety condition, the active portion 9 of the activating element 5 is abutted to the radial endrun portion 60 of the coupling element 4 located at the projection 15 of the coupling element 4.

In this condition, a lower appendage 9a of the active portion is intercepted by the projection 15.

In detail, the lower appendage 9a abuts against the radial intersection portion 16 and prevents a rotation of the active portion 9 (and therefore the activating element 5) towards the passage seating 8, i.e. towards the dispensing condition.

In other terms the cooperation between the projection 15 and the active portion 9 (or more accurately the inferior appendage 9a thereof) prevents a relative rotation of the two components coupled in an anticlockwise direction in the figures.

Obviously the rotation in the opposite direction (clockwise) is prevented by the cooperation of the active portion abutting against the abutting surface 60 defined by the radial endrun.

In this way the activating element 5, in the safety condition, is stably blocked to the coupling element 4 and relative rotations are not allowed.

Note that in this safety condition, the dispensing of the cryogenic substance is not enabled as the active portion 9 rests on the support portion 17 of the coupling element 4 and does not enable an axial nearing of the two bodies 4 and 5.

Figure 6:
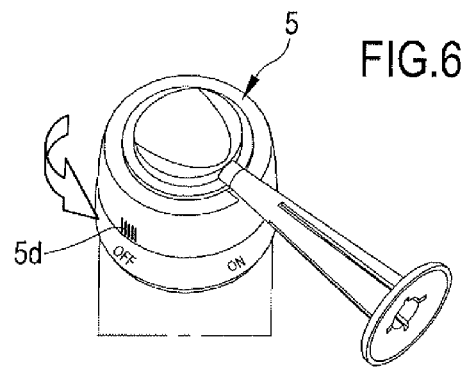
FIG. 6 is a partial perspective view of a dispenser, in accordance with the present invention, in an intermediate condition.
Figure 7:
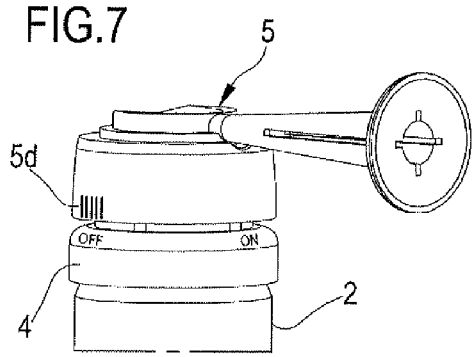
FIGS. 7 and 8 are partial perspective views of a dispenser, in accordance with the present invention, in a delivery condition.

The activating element 5 is further configured so as to define, in cooperation with the coupling element 4, at least an intermediate condition in which the activating element 5 is mobile in relation to the coupling element in rotation about the axis A substantially parallel to the expulsion direction E: the activating element 5, in the intermediate condition, can be displaced from the dispensing condition to the safety condition and vice versa (see the schematic representation in FIG. 6).

This intermediate condition occurs when the projection 15 and the lower appendage 9a of the active portion are disengaged and therefore anti-clockwise rotation of components 4 and 5 is enabled.

However, as long as the active portion 9 is not exactly at the seating 8, each relative axial translation between the bodies 4 and 5 is prevented and there cannot be any dispensing of cryogenic substance.

The active portion 9 of the activating element 5 comprises, non-limitingly, at least the lower appendage 9a, in detail constrained to and emerging from an internal lateral wall 5b of the housing compartment 5a and nearingly to the coupling element 4. As previously described, the lateral wall 18 of the coupling element (bearing the blocking portion and the passage seating 8) is arranged internally of the housing compartment 5a of the activating element 5; the lower appendage 9a of the active portion 9 emerges from the lateral internal wall 5b of the housing compartment 5a nearingly to the lateral wall 18 so that lateral wall 18 is interposed between the internal lateral wall 5b and the engaging portion 20 of the activating element (see the section view of FIG. 3 and the detail of FIG. 3A). In geometrical terms, the lower appendage 9a defines an interruption of the ribbing 19 emerging substantially perpendicularly to the internal lateral wall 5b of the housing compartment 5a between a first and a second lateral surface. The distance of the surfaces defines the thickness of the ribbing 19 which is smaller than the width of the passage seating 8.

As previously mentioned, the active portion 9 cooperates with both the blocking portion 7 and with the passage seating 8. In particular, as will be better described in the following, the ribbing 19 (active portion 9) of the activating element 5 is configured so as to slide internally of the passage seating 8 is configured so slide internally of the passage seating 8: for this reason the dimensions of the ribbing 19 are smaller than the corresponding dimensions of the seating 8 in the width direction.

Figure 4:
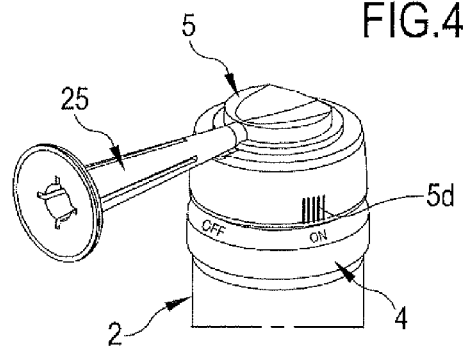
FIGS. 4 and 5 are partial perspective views of a dispenser, in accordance with the present invention, placed in a safe condition.

The lower appendage 9a of the activating element 5 substantially defines a radial intersection surface 13 and an axial intersection surface 14 which, in the safety condition (see for example FIGS. 4 and 5), are abutted respectively to the radial intersection portion 16 and to the support portion 17 of the coupling element 4. In the safety condition, the radial intersection portion 16 and the support portion 17 of the coupling element 4 are configured so as to prevent respectively the rotation and the axial translation of the activating element 5. In fact, the activating element 5, during the safety condition, is not mobile in relation to the coupling element 4.

In greater detail, the radial intersection portion 16 of the coupling element 4 defines a radial undercut with respect to the radial intersection surface 13 of the activating element 5: the radial intersection surface 13 of the activating element 5, during the safety condition, is abutted to the radial intersection portion 16 of the coupling element 4 and blocked in movement with respect thereto.

Regarding the axial intersection surface 14 of the activating element 5, at least in the safety condition the activating element 5 is abutted to the support portion 17 of the coupling element 4 so as to prevent the activating element 5, at least in the safety condition, from translating along the expulsion direction E nearingly to the container 2.

The impossibility of translation by the activating element 5 nearingly to the container 2 prevents the dispensing conduit 6 from pushing the body 39 internally of the container 2 so as to arrange the valve 3 in the passage condition. In fact, during the safety condition the valve 3 is not activatable and dispensing of the cryogenic substance C is not enabled.

As previously described, the activating element 5 and the coupling element 4 are configured so as to further define a dispensing condition in which the active portion 9 is slidingly mobile nearingly to the container 2. In this condition, the active portion 9 is at, and is inserted in the passage seating 8 (angularly offset with respect to the blocking portion 7) and can slide internally of the seating 8.

As previously described, the dispensing conduit 6 is resting on the portion 40 of the body 39: the nearing translation to the container 2 enables the abutting portion 62 of the conduit 6 to push the body 39 internally of the container 2 and arrange the valve 3 in the passage condition. In fact, in the dispensing condition, the axial sliding of the activating element 5 along the direction of expulsion E enables emission of the cryogenic substance C.

In the intermediate condition, the activating element 5 is mobile in rotation relatively to the coupling element 4 so as to enable passage from the safety condition to the dispensing condition and vice versa (see FIG. 6). In the intermediate condition, the axial intersection surface 14 of the activating element 5 is abutted on the support portion 17 of the coupling element 4 which prevents the activating element 5 from moving in a nearing direction to the container 2. In fact, in the intermediate condition, the activating element 5 can only rotate with respect to the coupling element 4 without being able to push the body 39 internally of the container 2 and consequently cause the activation of the valve 3.

To enable passage from the safety condition to the intermediate condition, the activating element 5 is configured so as to deform elastically, following the application of an external solicitation F (see FIG. 5) so as to allow decoupling between the active portion 9 of the activating element 5 (in particular the lower appendage (9*a*) and the blocking portion 7 of the coupling element 4.

In particular, the activating element 5, following the application of the external solicitation F, can be arranged in the intermediate condition and consequently pass from the safety condition to the dispensing condition.

As visible for example from FIGS. 4 to 8, the body 5*c* of the activating element 5 exhibits at least a thrust portion 5*d* located at a lateral external wall 5*e* of the body 5*c*. The thrust portion 5*d* is configured so as to receive the external solicitation F directed transversally to the expulsion direction E (transversal to the sliding direction S) and having an entering direction with respect to the housing compartment 5*a*; the thrust portion 5*d*, following the application of the external solicitation F, is configured so as to elastically deform at least a portion of the body 5*c* so as to allow distancing of the lower appendage 9*a* of the activating element 5 from the blocking portion 7 of the coupling portion 4 so as to allow decoupling thereof.

In fact, the distancing of the lower appendage 9*a* with respect to the lateral wall 18 enables radially freeing the intersecting portion 13 of the activating element 5 with respect to the intersecting portion 16 of the coupling element 4: in this way the last portion no longer defines a radial undercut for blocking the rotation of the activating element 5 which can be arranged in the intermediate condition and thereafter in the dispensing condition.

In the preferred condition illustrated in the figures of the drawings, the thrust portion 5*a* is angularly offset in relation to the active portion 9 with respect to the axis A; in particular it is offset by 90° with respect to the active portion 9.

The body 5*c* advantageously exhibits two thrust portions 5*d* positioned symmetrically to one another with respect to the axis A (a favourable condition for gripping and deforming the body 5*c*.

In this way the operator, acting with two fingers of the same hand, deforms the activating element 5 to bring it from a circular configuration to a helical configuration in which the lower appendage 9*a* (or the lower appendages 9*a* if there are two opposite) is at the larger axis of the ellipse, distancing and disengaging from the projection 15 of the coupling element and in that configuration being able to be rotated and disengaged definitively from the projection.

As previously described, the coupling element 4 comprises a radial endrun portion 60 which is positioned at the passage seating 8 and at the blocking portion 7. The portion 60 is configured so as to contact the active portion 9 of the activating element 5 when the activating element passes from the intermediate condition to the safety condition or dispensing condition. In fact, the portion 60 defines an endrun position which enables alignment of the active portion 9 with the passage seating 8 and with the blocking portion 7. In greater detail, the radial endrun portion 60 prevents the activating element 5 from rotating into an erroneous position, dealigned with the seating 8 and/or with the portion 7.

As previously described, the coupling element 4 further comprises an axial projection 61 (see FIG. 10) located on an upper support surface of the wall 18. This projection 61 is configured so as to contact the active portion 9 when the activating element 5 is in the intermediate condition and shortly prior to defining the dispensing element. The projection 61 represents, in fact, a step which enables the user to note the passage between the intermediate condition and the dispensing condition.

As already mentioned, a tooth might be additionally or alternatively present, emerging from the lateral wall 18 located at the seating 8 and with the aim of informing the user that the desired position has been reached.

As is visible from the figures, the dispenser 1 further comprises an applicator 25 engaged to the activating element 5 and configured so as to receive the cryogenic substance C in arrival from the dispensing conduit 6 and guide the cryogenic substance C towards the zone to be treated.

In structural terms, the applicator 25 exhibits a body 26 extending along a prevalent development direction between a first and a second end 27, 28. The applicator 25 is engaged, at the first end 27, to the activating element 5 and emerges from the lateral external wall 5*e* thereof in an exiting direction with respect to the housing compartment 5*a* of the activating element 5.

The applicator 25 exhibits a through-opening 29 along all the body 26 (from the first end 27 to the second end 28) which is in fluid communication with the dispensing conduit 6 of the activating element 5.

In particular, the opening 29 defines at the first and second end 27, 28, respectively a first and a second passage opening 31, 32.

The applicator 25 functions substantially as a diffuser: the first passage opening 31 defines a smaller passage area defined by the second passage opening 32. In particular, the opening 29 exhibits a cylindrical shape about a substantially parallel axis to the prevalent development direction of the applicator 25; the opening 29 exhibits a truncoconical shape having a growing passage section from the first end 27 in the direction of the second end 28. The shape of the applicator 25 is optimal for the flow concentration directly on the part to be treated.

It is useful to specify that for a correct application of the cryogenic substance C it is advisable to maintain a determined distance from the application zone. The elongate shape of the applicator 25 enables correctly distancing the outlet zone of the dispensing conduit 6 of the cryogenic substance C from the zone on which it is to be applied.

The applicator 25 can advantageously be realised, at least at the second end 28, with a transparent material enabling viewing of the zone to be treated also when the applicator 25 is in contact therewith. The transparency of at least part of the applicator 25 facilitates the viewing of the zone to be treated, in order to be able to perform the treatment with precision.

A preferred embodiment of the applicator 25 is reported in the figures, which comprises a support portion 63 that enables a correct positioning of the applicator 25 on the application zone during the dispensing step. In fact the support portion 63 comprises, non-limitingly, a disc emerging transversally with respect to the prevalent development direction of the body 26. In a preferred embodiment, illustrated in the figures, the support portion 63 exhibits a widened circular shape which substantially develops a platform for supporting the applicator 25 on the part to be treated, so that the dispenser 1 is maintained in a perpendicular position during the treatment, preventing swinging movements that are disadvantageous for the effectiveness of the treatment.

The figures relate to a preferred embodiment of the applicator 25 which further comprises at least a slit 30 arranged on the external lateral wall of the body 26 and which places the opening 29 in fluid communication 29 with the outside environment. The slit 30 is particularly useful in a case where the applicator 25 is placed in contact with the application zone: in this case the slit 30 functions as a discharge opening for optimizing the freezing effect of the cryogenic substance which enables maintaining the second end 28 of the body 26 supported during dispensing of the substance C.

In greater detail, the slit 30, located advantageously in the terminal part of the applicator 25 (substantially at the second end) is specially structured and predisposed to facilitate contact of the cryogenic substance C with the oxygen with the aim of more rapidly obtaining the freezing effect. In the figures, a non-limiting preferred embodiment of the applicator 25 is shown, exhibiting four slits 30 exhibiting an extension parallel to the prevalent development direction of the body 26 of the applicator 25; the slits 30 extend starting from the second end 28 nearingly to the first end of the applicator 25.

The slits 30 are advantageously distributed uniformly about the body 26 of the applicator 25 so as to allow uniform contact of the cryogenic substance C with the oxygen.

The applicator 25 is advantageously configured so as to removably engage the activating element 5: in this way different types of applicators 25 can be comprised, mountable on the activating element 5, having different geometrical and/or physical characteristics (for example the length, dimension of the opening and the material with which the applicator is realised). The removability of the applicator 25 makes the dispenser extremely flexible and adaptable to different zones to be treated, which can exhibit for example different dimensions. It is possible to include a series of applicators 25, adaptable to the dispenser 1, having different outlet diameters of the cryogenic substance, so as to precisely carry out the treatment of the various dimensions of the marks and/or lesions to be treated.

As regards the coupling, the applicator might be forced into the seating of the activating element or snap-removable engagements might be used, or the like.

Method for Dispensing Cryogenic Substances.

An object of the present invention is a method for dispensing cryogenic substances, in particular used for treatment/destruction of skin blemishes and/or bad or diseased skin tissue.

Figure 8:
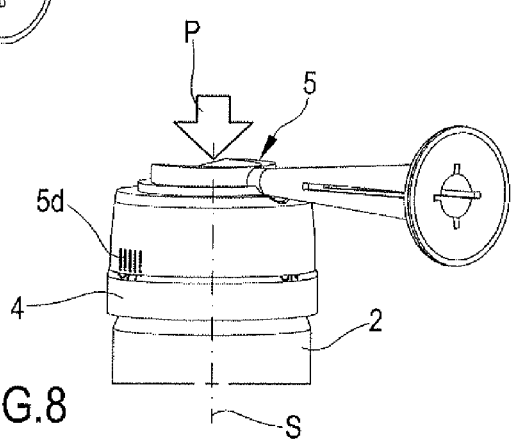

The dispensing method of the present invention includes at least a dispensing step in which the active portion 9 is slidingly mobile in the passage seating 8 along sliding direction S, substantially parallel to the expulsion direction E, nearingly to the container 2. The nearing along the expulsion direction E of the activating element relatively to the container 2 arranges the valve 3 of the container 2 in the passage condition so as to enable exit of at least a part of the cryogenic substance C from the opening 2a (this condition is illustrated in FIG. 8).

In greater detail the dispensing step includes a sub-step of sliding in the ribbing 19 internally of the passage seating 8. The nearing of the activating element 5 enables the abutting portion 62 of the dispensing conduit 6 to push the body 39 internally of the container 2. The dispensing step thus includes the sliding, according to an entering direction with respect to the container 2, both of the activating element 5 and the body 39: this causes activation of the valve 3 with a consequent arrangement thereof in the passage condition in which the cryogenic substance C can exit from the container 2.

As previously described, the body 39 of the valve 3 is pushed by an elastic element 43 able to maintain the valve 3 in the normally closed condition in which exit of the cryogenic substance C from the container 2 is not enabled. The dispensing step comprises a sub-step of pushing the activating element 5 nearingly to the container 2 directed on the opposite side to the resistant force provide by the elastic element 43. By applying a push P on the activating element 5 greater than the resistant force of the elastic element 43, the activating element 5 can be slid (consequently the body 39) along the sliding direction S and the valve 3 of the container 2 predisposed in the passage condition (see FIG. 8).

The method further comprises an intermediate movement step in which the activating element 5 is displaced relatively to the coupling element 4 by rotation about an axis A substantially parallel to the expulsion direction E (this step is schematized in FIG. 6).

During the step of intermediate movement the axial portion of intersection 14 of the activating element is abutted to an upper surface of the wall 18: this prevents the activating element 5 from sliding nearingly to the container and consequently activating the valve 3.

The intermediate movement step includes only relative rotation of the activating element 5 with respect to the coupling element 4: during this intermediated step the activating element 5 stays the same distance from the container 2 at all times.

The method further comprises at least a safety blocking step in which the active portion 9 of the activating element 5 is abutted to the blocking portion 7 of the coupling element 4 and is stably blocked to the coupling element 4. In fact, during the safety blocking step the activating element 5 is not mobile with respect to the coupling element 4, neither axially nor radially.

In greater detail, during the safety blocking step, the radial intersection surface 13 and the axial intersection surface 14 of the activating element 5 are abutted respectively to the radial intersection portion 16 and to the support portion 17 of the coupling element 4: the radial intersection portion 16 and the support portion 17 of the coupling element 4 respectively block the rotation and translation of the activating element 5.

The method comprises an unblocking step which comprises a step of elastically deforming at least a part of the activating element 5 following application of an external stress F. The elastic deformation step is configured such as to enable decoupling between the blocking portion 7 of the coupling element 4 and the active portion 9 of the activating element 5 when they are in the safety step such as to enable passage between the safety step and the intermediate step.

Figure 5:
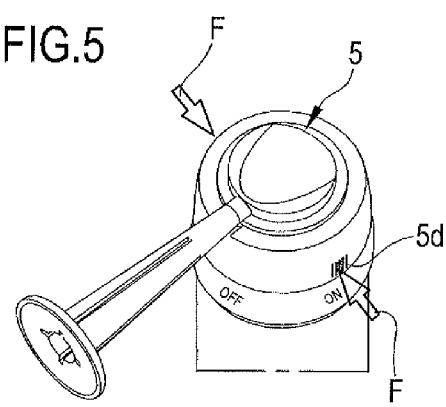

The elastic deformation step comprises application of the external solicitation F, directed transversally to the expulsion direction E and having an entering direction with respect to the activating element 5, on the thrust portion 5d (this step is schematically illustrated in FIG. 5); at least a part of the body 5c of the activating element 5, following application of the external solicitation F, elastically deforms so as to enable distancing and decoupling of the active portion 9 of the activating element 5 with respect to the blocking portion 7 of the coupling element 4.

As previously described, in the preferred embodiment that thrust portion 5d is angularly offset by 90% with respect to the active portion 9 relative to the expulsion direction E; the elastic deformation step includes application of the external solicitation F in an angularly offset point with respect to the position of the active portion 9 of the activating element 5.

During the elastic deformation step, the ribbing distances from the lateral wall 18 of the coupling element 4: following the distancing, in particular a radial distancing, the activating element 5 can rotate in relation thereto about the expulsion axis E.

The method further comprises a step of directing the cryogenic substance C in outlet from the dispensing conduit 6 and a preceding sub-step of predisposing the applicator 25 in fluid communication with the dispensing conduit 6 of the activating element 5.

The freezing of the zone to be treated is done by resting the support portion 63 directly on the skin, which facilitates the application of the cryogenic substance C perpendicularly to the zone to be treated, preventing swinging movements which facilitate treatment in oblique positions which would produce an asymmetric freezing, disadvantageous for the effectiveness of the treatment.

During the directing step, the applicator 25 enables distancing the dispensing conduit 6 from an application zone of the cryogenic substance C.

The method preferably includes application of the cryogenic substance C directly by resting the support portion 63 of the applicator 25 on the part to be treated, taking attention to centring the perimeter to be treated, with the pre-batched flow. The method advantageously includes consecutive dispensing established according to the lesion and the dimensions of the area to be treated; this enables expansion of the freezing-line from the centre towards the periphery, preventing swinging movements, up to producing a visible freezing-line on the skin which has to be at least 1 mm greater than the perimeter of the blemish and/or lesion to be eliminated.

Advantages of the Invention

The present invention enables important advantages to be attained with respect to the dispensers of cryogenic substances and dispensing methods of the substances known today.

As previously mentioned, cryogenic treatment requires special precautions as the state of the substance with which the treatment is performed can cause burns or, if dispensed on unsuitable zones for treatment, can cause grave lesions.

The above-described dispenser 1 comprises a safety system defined by the cooperation of the blocking portion 7 of the coupling element 4 and the active portion of the activating element 5. The safety system prevents the activating element 5 from causing accidental dispensing of cryogenic substance C.

The unblocking of the activating element 5 requires a step of elastic deformation of at least a part of the body 5c of the activating element and a subsequent rotation thereof so as to bring it into the dispensing condition. These operations certainly cannot occur accidentally, which guarantees the dispenser 1 will prevent undesired dispensing.

The dispenser 1 comprises a valve 3 exhibiting a pre-chamber 2d which enables dispensing predetermined quantities of cryogenic substance smaller than the total quantity present in the container 2. This characteristic enables supplying suitable pre-batched quantities which can prevent excessive dispensing and/or wasting of cryogenic substance.

Further, the dispenser 1 comprises an applicator 25 that can enable correcting directing of the cryogenic substance C on the application zone and further a correct distancing thereof from the outlet of the dispensing conduit 6. In particular, the applicator 25 is made with the right height which enables performing the treatment from the ideal distance for facilitating expansion of the freezing front-line from the centre towards the periphery so as to optimize the effectiveness of the treatment.

The terminal part of the applicator 63 has a circular disc-shape, specially structured to be used as a "platform" for suitable resting the applicator on the zone to be treated, so that during the treatment the device is maintained in a perpendicular position, prevent swinging movements, which would produce an asymmetric freezing that is disadvantageous for the effectiveness of the treatment.

LEGEND 1 dispenser of cryogenic substances
2 container
2a container opening
2b engaging portion of the container 2
2c general chamber
2d pre-chamber
3 valve
4 coupling element
5 activating element
5a housing compartment
5b internal lateral wall of through housing 5a
5c body
5d thrust portion
5e external lateral wall
6 dispensing conduit
7 blocking portion
8 passage seating
9 active portion
9a lower appendage
10 first engaging portion of the coupling element 4
11 second engaging portion of the coupling element 4
12 projection of the second engaging portion 11
13 radial intersection surface of the activating element 5
14 axial intersection surface of the activating element 5
15 projection of the coupling element 4
16 radial intersection portion of the coupling element 17 support portion of the coupling element
18 lateral part of the coupling element 4
19 ribbing of the activating element 5
20 engaging portion of the activating element 5
21 abutment
22 inlet of pre-chamber 2d
23 outlet of pre-chamber 2d
24 valve
25 applicator
26 body of applicator 25
27 first end of the applicator 25
28 second end of the applicator 25
29 opening
30 slit
31 first opening
32 second opening
33 constraining element
34 opening of the constraining element
35 first end
36 second end
37 first axial abutment
38 second axial abutment
39 elongate body of the valve 3
40 first portion
41 second portion
42 abutment
43 further abutment
42a elastic element
44 outlet line of the valve 3
45 first opening
46 second opening
47 batching device
48 support portion
49 housing seating
50 closing portion
51 tab
52 lateral wall of the batching device 47
53 end portion of the batching device 47
54 abutment
55 fold
56 seal element
57 projection
58 abutting element
59 further projection
60 radial endrun portion
61 axial portion
62 abutting portion
63 support portion
A axis
C cryogenic substance
E expulsion direction
F external solicitation
S sliding direction

The invention claimed is:

1. A dispenser of cryogenic substances comprising:
at least a pressurised container configured such as to contain a predetermined quantity of cryogenic substance, the container exhibiting at least an opening suitable for enabling exit of the cryogenic substance along an expulsion direction, the container comprising a valve active at the opening and configured such as to be arranged in a normally closed condition in which it prevents the exit of the cryogenic substance from the opening, the valve being further configured such as to be arranged, following an activating operation thereof, in a passage condition in which the valve enables exit of the cryogenic substance,
at least a coupling element comprising a first engaging portion able to stably constrain the coupling element to the container at the opening, the coupling element comprising a second engaging portion emerging from the first engaging portion distancingly with respect thereto, the second engaging portion comprising at least a blocking portion and at least a passage seating angularly, wherein the at least a blocking portion is offset to the at least a passage seating and the offset is with respect to an axis that is parallel to the expulsion direction,
at least an activating element cooperating with the second engaging portion of the coupling element such that the coupling element is interposed between the container and the activating element, the activating element comprising a dispenser conduit in fluid communication with the opening of the container and configured such as to enable emission of the cryogenic substance towards the external environment, the activating element further comprising an active portion able to cooperate with the blocking portion and the passage seating of the coupling element,
wherein the activating element is configured such as to define, in cooperation with the coupling element, at least following operating conditions:
at least a dispensing condition in which the active portion of the activating element is at the passage seating, the activating element, in the dispensing condition, being translatable along a sliding direction nearingly to the container, the activating element, following the nearing along the sliding direction towards the container, being configured such as to arrange the valve in the passage condition and consequently enabling exit of at least a part of the cryogenic substance from the opening,
at least a safety condition in which a lower appendage of the activating element is located at the at least a blocking portion of the coupling element, the activating element, in the safety condition, being stably blocked to the coupling element preventing relative rotations and axial slidings of the activating element with respect to the coupling element, wherein while the activating element is in the safety condition, the activating element is both prevented from movement along the axis and prevented from rotating about the axis by the blocking portion of the coupling element;
at least an intermediate condition in which the activating element is mobile relatively to the coupling element by rotation about the axis parallel to the expulsion direction, the activating element, in the intermediate condition, being mobile from a dispensing condition to a safety condition and vice versa,
the activating element being configured such as to elastically deform, following application of an external stress, such as to enable, at least in the safety condition, the decoupling between the lower appendage of the activating element and the blocking portion of the coupling element, the activating element, following the application of the external stress, being arrangeable in the intermediate condition and consequently being able to pass from the safety condition to at least a dispensing condition,
wherein the activating element comprises a body having at least two thrust portions located at an external lateral wall of the body, the thrust portion being configured to receive the external stress directed transversally to the expulsion direction;

wherein the at least two thrust portions being configured to elastically deform, in response to application of the external stress, at least a portion of the body to enable distancing of the active portion of the activating element with respect to the blocking portion of the coupling element to enable decoupling thereof; and wherein the at least two thrust portions are arranged symmetrically with respect to the axis parallel to the expulsion direction.

2. The dispenser of claim 1, wherein the at least two thrust portions are angularly offset relative to the active portion with respect to the axis.

3. The dispenser of claim 2, wherein the at least two thrust portions are angularly offset by 90° relative to the active portion with respect to the axis.

4. The dispenser of claim 2, wherein the coupling element exhibits a shape having a cylindrical symmetry about the expulsion direction, the first engaging portion being stably coupled with an engaging portion of the container positioned at the opening, the second engaging portion being configured such as to stably constrain the activating element to the coupling element, the second engaging portion of the coupling element being connected to the first engaging portion of the coupling element and emerging distantly with respect thereto, the second engaging portion of the coupling element comprising the blocking portion which exhibits at least a projection defining at least a radial intersection portion and a support portion, and wherein the body of the activating element defines a housing compartment delimited by an internal lateral wall and containing at least a part of the second engaging portion of the coupling element, the active portion of the activating element comprising at least a projection emerging from the internal lateral wall of the housing compartment nearingly to the coupling element, the projection of the activating element defining at least another radial intersection portion and an axial intersection portion, wherein the radial intersection portion and the axial intersection portion of the activating element, during the safety condition, are abutted respectively to the radial intersection portion and the support portion of the coupling element, in the safety condition the radial intersection portion and the support portion of the coupling element being configured such as respectively to prevent the rotation and translation of the activating element, and wherein the radial intersection portion of the coupling element defines a radial undercut with respect to the radial intersection portion of the activating element, the radial intersection portion of the activating element, during the safety condition, being abutted to the radial intersection portion of the coupling element and blocked in movement with respect thereto.

5. The dispenser of claim 4, wherein the axial intersection portion of the activating element is abutted to the support portion of the coupling element, at least in the safety condition, and wherein the support portion of the coupling element defines an axial undercut able to prevent the activating element, at least in the safety condition, from translating along the expulsion direction nearingly to the container.

6. The dispenser of claim 5, wherein the axial intersection portion of the activating element is abutted to the support portion of the coupling element in the safety condition and in the intermediate condition.

7. The dispenser of claim 4, wherein the passage seating of the coupling element is arranged on the second engaging portion thereof and extends parallel to the expulsion direction, the passage seating being angularly offset with respect to the blocking portion of the coupling element with respect to the expulsion direction, the passage seating being configured such as to enable passage of the axial intersection portion of the activating element, during the dispensing condition, and therefore the sliding of the activating element nearingly to the container.

8. The dispenser of claim 4, wherein the second engaging portion of the coupling element comprises at least a lateral wall extending parallel to the expulsion direction, the radial intersection portion of the coupling element emerging radially from the lateral wall towards the internal lateral wall of the housing compartment, and wherein the support portion of the coupling element is defined by at least a portion of the free end surface of the lateral wall located on an opposite side with respect to the first engaging portion of the coupling element, and wherein the projection of the activating element comprises at least a rib emerging parallel to the internal lateral wall of the housing compartment nearingly to the coupling element, the rib defining the radial intersection portion and the support portion of the activating element.

9. The dispenser of claim 1, wherein the container, during each dispensing condition, is configured such as to dispense only a predetermined discrete quantity of cryogenic substance less than the total quantity of cryogenic substance present internally of the container, and wherein the container comprises a general chamber configured such as to contain a predetermined quantity of cryogenic substance, the container further comprising a pre-chamber exhibiting at least an inlet for setting the general chamber in fluid communication with the pre-chamber, the pre-chamber further exhibits at least an outlet for setting the pre-chamber in fluid communication with the opening of the container, the container comprising at least a valve operatively active on the inlet and on the outlet of the pre-chamber, the valve, in the dispensing condition, being configured such as to set the pre-chamber in fluid communication with the opening of the container and to prevent the passage of fluid between the general chamber and the inlet, the valve of the container, in the dispensing condition, being configured such as to enable emission of the predetermined quantity of cryogenic substance present in the pre-chamber of the opening of the container, and wherein the valve, in the safety condition and/or in the intermediate condition, is configured such as to set in fluid communication the pre-chamber with the general chamber and prevent the passage of fluid between the pre-chamber and the opening of the container.

10. The dispenser of claim 2 comprises at least an applicator having a body extending along a prevalent development direction between a first and a second end, the applicator being removably engaged, at the first end, to the activating element and emerging from the external lateral wall thereof in an exiting direction with respect to the housing compartment of the activating element, and wherein the applicator exhibits a through-opening extending internally of all the body from the first end to the second end, the dispensing conduit of the activating element being in fluid communication with the opening of the applicator, the applicator, in the dispensing condition, being configured such as to guide the cryogenic substance arriving from the container towards the outside environment.

11. The dispenser of claim 1, wherein the coupling element comprises two blocking portions arranged symmetrically with respect to the expulsion direction, and wherein the coupling element further comprises two passage seatings arranged symmetrically with respect to the expulsion direction, the blocking portion and the passage seatings being angularly offset with respect to one another with respect to the expulsion direction.

12. The dispenser of claim 11, wherein the blocking portion is angularly offset by 90° from the passage seatings with respect to the expulsion direction.

* * * * *